(12) United States Patent
Kumada et al.

(10) Patent No.: US 9,701,760 B2
(45) Date of Patent: Jul. 11, 2017

(54) PEPTIDE HAVING AFFINITY FOR SILICON NITRIDE (SI₃N₄), AND USE THEREFOR

(71) Applicant: National University Corporation Kyoto Institute of Technology, Kyoto (JP)

(72) Inventors: Yoichi Kumada, Kyoto (JP); Michimasa Kishimoto, Kyoto (JP); Takeru Otsuka, Kyoto (JP)

(73) Assignee: National University Corporation Kyoto Institute of Technology, Kyoto (JP)

( * ) Notice: Subject to any disclaimer, the term of this patent is extended or adjusted under 35 U.S.C. 154(b) by 0 days.

(21) Appl. No.: 14/378,433

(22) PCT Filed: Feb. 12, 2013

(86) PCT No.: PCT/JP2013/053290
§ 371 (c)(1),
(2) Date: Aug. 13, 2014

(87) PCT Pub. No.: WO2013/122061
PCT Pub. Date: Aug. 22, 2013

(65) Prior Publication Data
US 2015/0038675 A1   Feb. 5, 2015

(30) Foreign Application Priority Data

Feb. 13, 2012 (JP) .................................. 2012-028681

(51) Int. Cl.

| C07K 17/14 | (2006.01) |
| C07K 14/245 | (2006.01) |
| C07K 7/06 | (2006.01) |
| C07K 7/08 | (2006.01) |
| C12N 9/04 | (2006.01) |
| C12N 11/14 | (2006.01) |

(52) U.S. Cl.
CPC ............... *C07K 17/14* (2013.01); *C07K 7/06* (2013.01); *C07K 7/08* (2013.01); *C07K 14/245* (2013.01); *C12N 9/0006* (2013.01); *C12N 11/14* (2013.01); *C07K 2319/00* (2013.01); *C07K 2319/23* (2013.01)

(58) Field of Classification Search
None
See application file for complete search history.

(56) References Cited

U.S. PATENT DOCUMENTS

| 5,955,335 A | 9/1999 | Thust et al. |
| 2007/0099304 A1 | 5/2007 | Puente et al. |
| 2008/0154024 A1 | 6/2008 | Kirimura et al. |
| 2009/0098578 A1 | 4/2009 | Kuroda et al. |
| 2009/0118142 A1 | 5/2009 | Kuroda et al. |
| 2011/0045538 A1 | 2/2011 | Kumada et al. |
| 2015/0017454 A1* | 1/2015 | Li .................... H01L 21/31053 428/446 |

FOREIGN PATENT DOCUMENTS

| CN | 1782709 | 6/2006 |
| JP | 2007-127631 A | 5/2007 |
| JP | 2009-136280 A | 6/2009 |
| JP | 2011-168505 A | 9/2011 |
| JP | WO 2012090789 A1 * | 7/2012 ......... G01N 33/6803 |
| WO | 2004/081206 | 9/2004 |

(Continued)

OTHER PUBLICATIONS

Straus, Joshua et al "Bindign, inactivation, and adhesion forces between antimicrobial peptide ceropin P1 and pathogenic *E. coli*." Colloids and Surfaces B (2010) 75 p. 156-164.*
Arai, K et al, "Primary structure of elongation factort tu from *Escherichia coli*." Proc. Natl. Acad. Sci. USA (1980) 77(3) p. 1326-1330.*
Rosso, Michel et al, "Protein repellent silicon nitride surfaces: uv-induced formation of oligoethylene oxide monolayers." ACS Appl. Mater. Interfaces (2011) 3 p. 697-704.*
Giannoulis, Constantina S. and Desai, Tejal A.; "Characterization of proteins and fibroblasts on thin inorganic films." J. Mat. Sci. (2002) 13 p. 75-80.*
Yampolsky, Lev Y. and Stoltzfus, Arlin, "The exchangeability of amino acids in proteins." Genetics (2005) 170 p. 1459-1472.*
Machine translation of Ikeda et al, WO 2012090789.*

(Continued)

*Primary Examiner* — Fred Reynolds
(74) *Attorney, Agent, or Firm* — Casimir Jones, S.C.; David W. Staple

(57) ABSTRACT

The purpose of the present invention is to provide: a peptide having an affinity for silicon nitride; a polynucleotide encoding the peptide; an expression vector for expressing the peptide having an affinity for silicon nitride; an expression vector for expressing a peptide fusion protein that comprises the peptide having an affinity for silicon nitride and a target protein; a transformant obtained by introducing the expression vector into a host cell; a peptide fusion protein obtained from the transformant; a silicon nitride substrate to which a peptide having an affinity for silicon nitride has been bonded; a method for immobilizing a target protein to a silicon nitride substrate; a composition for immobilizing a target protein to a silicon nitride substrate, the composition comprising a peptide having an affinity for silicon nitride; and a linker for immobilizing a target protein to a silicon nitride substrate, the linker comprising a peptide having an affinity for silicon nitride. The invention involves a peptide having an affinity for silicon nitride, the peptide comprising (1-1) a peptide having the amino acid sequence of one of SEQ ID NOS: 1, 2 and 23 to 27, (1-2) a peptide that has an affinity for silicon nitride and comprises an amino acid sequence obtained by deleting, adding, and/or substituting one or more amino acids in one of the amino acid sequences indicated in (1-1), or a fragment of one of the peptides.

3 Claims, 5 Drawing Sheets

(56) References Cited

FOREIGN PATENT DOCUMENTS

| WO | 2007/055288 A1 | 5/2007 |
|---|---|---|
| WO | 2009/101807 A1 | 8/2009 |
| WO | 2012/090789 A1 | 7/2012 |

OTHER PUBLICATIONS

DeCarlo, K. J., "Silicon nitride synthesis." Ceramic Industry (2013) available online at http://www.ceramicindustry.com/articles/93163-silicon-nitride-synthesis).*

The web page of Harper college http://www.harpercollege.edu/tm-ps/chm/100/dgodambe/thedisk/bloodbuf/zback2.htm, downloaded Jul. 13, 2016.*

Abu-Lail, Nehal I. and Camesano, Terri A., "Specific and nonspecific interaction forces between *Escherichia coli* and silicon nitride, determined by poisson statistical analysis." Langmuir (2006) 22 p. 7296-7301.*

Corchero, Jose Luis et al, "Cell lysis in *Escherichia coli* cultures stimulates growth and bio-synthesis of recombinant protein in surviving cells." Microbiol. Res. (2001) 156 p. 13-18.*

Alksne, L.E. et al, "Identification and analysis of bacterial protein secretion inhibitors using a seca-lacz reporter fusion system." Antimicrob. Agents Chemother. (2000) 44(6) p. 1418-1427.*

2005 memo from the directors regarding nucleic acid and peptide claim interpretation.*

Abstracts of Annual Meeting of the Society of Chemical Engineers, "Isolation of peptide having affinity for Si3N4 substrate using proteomic analysis," Japan, 2012, vol. 77, p. 49 (B109), English Translation.

Abstracts of the Annual Meeting of the Society for Biotechnology, "Screening of Si3N4-binding peptides by proteome analysis technologies," Japan, 2011, vol. 63, p. 148 (2Ep20), English Translation.

Annual Report of the Murata Science Foundation, 2007, No. 21, pp. 167-172.

Kumada Y., "Development of Protein Immobilization Method by Use of Polystyrene-Binding Peptide," Polymers, 2011, vol. 60, No. 10, pp. 751-752.

Willett et al., "Differential adhesion of amino acids to inorganic surfaces," Proceedings of the National Academy of Sciences of the United States of America, 2005, vol. 102, No. 22, pp. 7817-7822.

GENESEQ Accession No. AEJ25911, Elongation factor Tu fragment SEQ ID No. 387, Sep. 21, 2006, 2 pages.

Knudsen et al., One-Step Purification of *E. coli* Elongation Factor Tu, Biochemistry International, 1992, 28:353-362.

Kumada et al., Identification and characterization of peptide fragments for the direct and site-specific immobilization of function proteins on the surface of silicon nitride, J Biotech, 2014, 184:103-110.

Maisonneuve et al., Rules Governing Selective Protein Carbonylation, PLoS One, 2009, 4:e7269.

Sarikaya et al., Molecular biomimetics: nanotechnology through biology, Nature Materials, 2003, 2:577-585.

Supplementary Partial European Search Report, mailed Feb. 24, 2016, for EP 13749185.8, 5 pages.

Jacenek et al., Proteomic profiling of L-cysteine induced selenite resistance in *Enterobacter* sp. YSU, Proteome Sci. 2009; 7:30.

Chinese Office Action dated Sep. 26, 2016 for CN Patent Application No. 201380009283.X, 16 pages, partial translation only.

* cited by examiner

US 9,701,760 B2

PEPTIDE HAVING AFFINITY FOR SILICON NITRIDE (SI$_3$N$_4$), AND USE THEREFOR

This application is a national stage of International Application No. PCT/JP2013/053290, filed Feb. 12, 2013, which claims priority to Japanese Application No. 2012-028681, filed Feb. 13, 2012, both of which are incorporated by reference herein in their entireties for any purpose.

TECHNICAL FIELD

The present invention relates to a peptide having an affinity for silicon nitride (Si$_3$N$_4$), and the use of the peptide.

BACKGROUND ART

Conventionally, the following technique has been used in various fields, such as clinical examinations, drug discovery research, environmental monitoring, and biochemistry. That is, immobilizing proteins, nucleic acids, sugar chains, cells, etc., to a substrate, and making use thereof to detect, quantify, analyze, etc., a desired substance. This technique is actively studied even today in order to achieve highly accurate and efficient detection, quantification, analysis, and the like.

For example, when proteins, such as enzymes and/or antibodies, are immobilized to a substrate, and the desired substance is detected by using an enzyme reaction or an antigen-antibody reaction with the immobilized proteins, in order to achieve detection with high accuracy and high efficiency, it is important to immobilize the proteins to a substrate while sufficiently maintaining the activity thereof. Aiming to perform such immobilization, a polystyrene affinity peptide that allows the protein to be immobilized to a polystyrene substrate has been reported (Patent Literature 1). It was confirmed that the activity of the proteins, such as enzymes and/or antibodies, was sufficiently maintained even after they had been immobilized to a polystyrene substrate.

Furthermore, as another peptide, an affinity peptide has been reported that can specifically and firmly immobilize a protein to a polycarbonate substrate or a polymethylmethacrylate substrate (Patent Literature 2).

Silicon nitride (Si$_3$N$_4$), which is used as one of such substrates, is also useful as a semiconductor material. Therefore, if a protein can be desirably immobilized to silicon nitride, further development of techniques utilizing a silicon nitride substrate can be expected. However, in examining the interaction between the surface of an inorganic substance and biomolecules, it has been reported that individual amino acids, such as histidine or arginine, adhere to the surface of silicon nitride (Non-patent Literature 1); however, no peptides having an affinity for a silicon nitride substrate have yet been disclosed.

CITATION LIST

Patent Literature

[PTL 1] WO2009/101807 A1
[PTL 2] JP2011-168505A

Non-Patent Literature

[NPL 1] R. L. Willett, et al. "Differential adhesion of amino acids to inorganic surfaces", Proc Natl Acad Sci USA., Vol. 102, no. 22, p. 7817-7822.

SUMMARY OF INVENTION

Technical Problem

The present invention aims to provide a peptide having an affinity for silicon nitride (Si$_3$N$_4$). The present invention further aims to provide a polynucleotide encoding a peptide having an affinity for silicon nitride. The present invention also aims to provide an expression vector for expressing a peptide having an affinity for silicon nitride, the expression vector comprising the polynucleotide. Furthermore, the present invention aims to provide an expression vector for expressing a peptide fusion protein comprising a peptide having an affinity for silicon nitride and a target protein, the expression vector further comprising a polynucleotide that encodes the target protein. The present invention also aims to provide a transformant obtained by transforming a host cell by introducing an expression vector thereinto, and/or a peptide fusion protein obtained from the transformant. Furthermore, the present invention provides a silicon nitride substrate to which a peptide having an affinity for silicon nitride has been bonded, and a method for immobilizing a target protein to a silicon nitride substrate. The present invention also aims to provide a composition for immobilizing a target protein to a silicon nitride substrate, the composition comprising a peptide having an affinity for silicon nitride, a linker for immobilizing a target protein to a silicon nitride substrate, the linker comprising a peptide having an affinity for silicon nitride, and use of the peptide having an affinity for silicon nitride for immobilizing the target protein to a silicon nitride substrate.

Means for Solving the Problem

The present inventors conducted extensive research to solve the above problems and found a peptide having an affinity for silicon nitride (Si$_3$N$_4$). The present invention has been accomplished based on this finding.

The present invention provides the following:

Item 1. A peptide having an affinity for silicon nitride, comprising a peptide of (1-1) or (1-2), or a fragment thereof;
(1-1) a peptide having the amino acid sequence represented by any one of SEQ ID NOS: 1, 2 and 23 to 27;
(1-2) a peptide that has an affinity for silicon nitride and comprises an amino acid sequence in which one or more amino acids are deleted, substituted, and/or added in the amino acid sequences of (1-1).

Item 2. The peptide having an affinity for silicon nitride according to Item 1, wherein the fragment comprises 6 to 77 amino acid residues.

Item 3. The peptide having an affinity for silicon nitride according to Item 1 or 2, wherein the fragment is a peptide having the amino acid sequence represented by any one of SEQ ID NOS: 3 to 11 and 28 to 35.

Item 4. A polynucleotide encoding the peptide having an affinity for silicon nitride of any one of Items 1 to 3.

Item 5. The polynucleotide according to Item 4, wherein the polynucleotide is represented by any one of SEQ ID NOS: 12 to 22 and 36 to 48.

Item 6. An expression vector for expressing a peptide having an affinity for silicon nitride, the expression vector comprising the polynucleotide of Item 4 or 5.

Item 7. An expression vector for expressing a peptide fusion protein comprising the peptide having an affinity for silicon nitride of any one of Items 1 to 3 and a target protein, the expression vector comprising the polynucleotide of Item 6 and a polynucleotide encoding the target protein linked to the polynucleotide.

Item 8. A transformant obtained by transforming a host cell by introducing the expression vector of Item 7 into the host cell.

Item 9. A peptide fusion protein comprising the peptide having an affinity for silicon nitride of any one of Items 1 to 3 and a target protein, the peptide fusion protein being obtainable from the transformant of Item 8.

Item 10. A silicon nitride substrate to which the peptide having an affinity for silicon nitride of any one of Items 1 to 3 is bonded.

Item 11. The silicon nitride substrate according to Item 10, wherein the target protein is immobilized to a silicon nitride substrate via a peptide having an affinity for silicon nitride.

Item 12. A method for immobilizing a target protein to a silicon nitride substrate comprising:
contacting the peptide having an affinity for silicon nitride of any one of Items 1 to 3 introduced into the target protein with a silicon nitride substrate.

Item 13. The immobilizing method according to Item 12, wherein the peptide having an affinity for silicon nitride contacted with the silicon nitride substrate constitutes a peptide fusion protein obtained by using the vector of Item 7 or the transformant of Item 8.

Item 14. A method for immobilizing a target protein to a silicon nitride substrate comprising:
bonding a peptide having an affinity for silicon nitride bonded to the silicon nitride substrate of Item 10 with the target protein.

Item 15. A composition for immobilizing a target protein to a silicon nitride substrate, the composition comprising the peptide having an affinity for silicon nitride of any one of Items 1 to 3.

Item 16. A linker for immobilizing a target protein to a silicon nitride substrate, the linker comprising the peptide having an affinity for silicon nitride of any one of Items 1 to 3.

Item 17. Use of the peptide having an affinity for silicon nitride of any one of Items 1 to 3 for immobilizing a target protein to a silicon nitride substrate.

Advantageous Effect of the Invention

The peptide of the present invention has an affinity for silicon nitride and can therefore easily immobilize to a silicon nitride substrate via the peptide. In particular, the peptide having an affinity for silicon nitride of the present invention makes it possible to immobilize the target protein with high density. The peptide having an affinity for silicon nitride of the present invention also allows the target protein to be immobilized to a silicon nitride substrate while maintaining the activity of the target protein. The peptide having an affinity for silicon nitride of the present invention further allows the target protein to be immobilized to a silicon nitride substrate while controlling the uniformity of the target protein orientation.

As described above, the present invention can achieve densification, activation, and highly controlled orientation of the target protein in the silicon nitride substrate. This indicates that the present invention allows the target protein to be immobilized to a silicon nitride substrate via the peptide having an affinity for silicon nitride in a highly accurate and highly efficient manner. Furthermore, the present invention allows a substance having an interaction with the target protein to bond to a silicon nitride substrate via the peptide having an affinity for silicon nitride in a highly accurate and highly efficient manner. Therefore, the peptide of the present invention is useful as a linker for immobilizing the target protein to a silicon nitride substrate.

By using the polynucleotide, vector, and/or transformant of the present invention, the peptide fusion protein comprising the peptide having an affinity for silicon nitride and the target protein of the present invention can be easily prepared.

The silicon nitride substrate to which a peptide having an affinity for silicon nitride has been bonded, the method for immobilizing the target protein to a silicon nitride substrate, and the composition for immobilizing the target protein to the silicon nitride substrate of the present invention allow the target protein to be immobilized to a silicon nitride substrate in a highly dense manner while sufficiently maintaining target protein activity, and while also uniformly controlling target protein orientation. This allows the target protein to be immobilized to a silicon nitride substrate in a highly accurate and efficient manner, and a desired substance having an interaction with the target protein to be bonded in a highly accurate and efficient manner.

As described above, the present invention makes it possible to detect, quantify, analyze, etc., a desired substance in a highly accurate and efficient manner, improving techniques in various analytical means, such as biochips.

DESCRIPTION OF EMBODIMENTS

Figure 1:
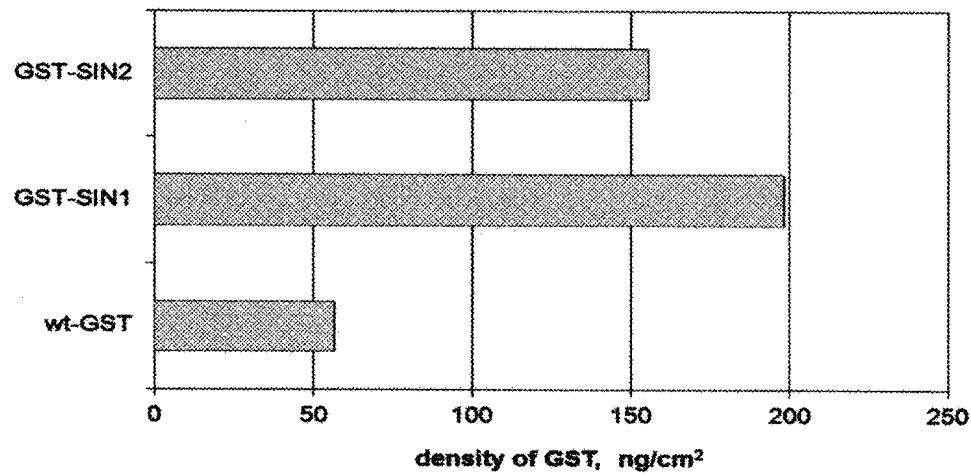
FIG. 1 indicates that the peptides represented by SEQ ID NOS: 1 and 2 have an affinity for a silicon nitride substrate.

The present invention is explained below.
1. Peptide Having an Affinity for Silicon Nitride The present invention provides a peptide having an affinity for silicon nitride. The peptide having an affinity for silicon nitride of the present invention comprises a peptide of (1-1) or (1-2), or a fragment thereof:

(1-1) a peptide having the amino acid sequence represented by any one of SEQ ID NOS: 1, 2 and 23 to 27;

(1-2) a peptide that has an affinity for silicon nitride and comprises an amino acid sequence in which one or more amino acids are deleted, substituted, and/or added in the amino acid sequences of (1-1).

In the present invention, peptide refers to a peptide comprising two or more amino acid residues bonded by a peptide bond, including those referred to as oligopeptides, polypeptides, and proteins, depending on the number of amino acid residues.

In the peptide of (1-2), the scope of the term "one or more" is not limited as long as the peptide has an affinity for silicon nitride. The number of peptides is, for example, 1 to 15, preferably 1 to 10, more preferably 1 to 5, furthermore preferably 1 to 4, particularly preferably 1 to 3, and yet more particularly preferably 1 or 2. In a specific amino acid sequence, a technique for deleting, substituting, and/or adding one or more amino acids is known.

An example of a peptide having such a deletion, addition, and/or substitution is a peptide having an amino acid sequence with 50% or more identity to the amino acid sequence represented by any one of SEQ ID NOS: 1, 2 and 23 to 27, and having an affinity for silicon nitride. The peptide has identity to the amino acid sequence of generally 70% or more, preferably 80% or more, more preferably 90% or more, furthermore preferably 95% or more, particularly preferably 97% or more, and yet particularly preferably 98% or more.

The peptides of the present invention are not limited by the following examples. Examples of the peptide described in (1-2) include those in which one or more amino acids are deleted, added, and/or substituted in the amino acid sequences represented by any one of SEQ ID NOS: 1, 2 and 23 to 27, with at least one amino acid sequence other than those represented by SEQ ID NOS: 3 to 11 and 28 to 35, and a peptide having an affinity for silicon nitride. Other examples of the peptide described in (1-2) above include those in which one or more amino acids are deleted, added, and/or substituted in the amino acid sequence represented by SEQ ID NO.: 1, with at least one amino acid sequence other than those represented by SEQ ID NOS: 3 to 5, and a peptide having an affinity for silicon nitride. Further examples of the peptide described in (1-2) above include those in which one or more amino acids are deleted, added, and/or substituted in the amino acid sequence represented by SEQ ID NO.: 2, with at least one amino acid sequence other than those represented by SEQ ID NOS: 6 to 11, and a peptide having an affinity for silicon nitride; those in which one or more amino acids are deleted, added, and/or substituted in the amino acid sequence represented by SEQ ID NO.: 23, with at least one amino acid sequence other than those represented by SEQ ID NOS: 28 to 30, and a peptide having an affinity for silicon nitride; and those in which one or more amino acids are deleted, added, and/or substituted in the amino acid sequence represented by SEQ ID NO.: 24, with at least one amino acid sequence other than those represented by SEQ ID NOS: 31 to 35, and a peptide having an affinity for silicon nitride.

The fragment of the peptide of (1-1) or (1-2) is also not limited as long as it is a fragment of the peptide of (1-1) or (1-2) described above and the fragment has an affinity for silicon nitride. Examples of the fragment include those comprising 6 to 77 amino acid residues, preferably 6 to 30 amino acid residues, and more preferably 6 to 15 amino acid residues, the fragment having an affinity for silicon nitride.

The fragment is not particularly limited by the following examples, which include a peptide having an affinity for silicon nitride and having the amino acid sequence represented by any one of SEQ ID NOS: 3 to 11 and 28 to 35. The present invention is also not particularly limited by the following examples, and the fragment may be a peptide in which the amino acid sequence represented by any one of SEQ ID NOS: 3 to 11 and 25 to 35 is repeated 2 or more times, and that has an affinity for silicon nitride.

Here, the term "having an affinity for silicon nitride" is not particularly limited as long as the peptide and a silicon nitride without surface modification can be directly bonded. The bonding conditions may be suitably selected depending on the types of the peptide used, the properties of the target protein to be immobilized to the silicon nitride substrate via the peptide, or depending on the properties of the desired substance having an interaction with the target protein. For example, the bonding (incubation) conditions utilized in the Examples described below may be employed, or a person skilled in the art may suitably select the conditions with reference to those described in the Examples. For example, the peptide can be bonded to a silicon nitride substrate by bringing any solution, such as a buffer solution comprising the peptide (e.g., a PBS solution), into contact with the silicon nitride substrate for a certain period of time. The PBS used in the Examples described later contain 10×PBS (NaCl 1.38 M (80.8 g), KCl 27 mM (2 g), $Na_2HPO_4 \cdot 12H_2O$ 80 mM (29 g), and $KH_2PO_4$ 15 mM (2 g)), diluted to a total volume of 1 L using ion-exchanged water and having its pH adjusted to 7.4 with HCl. As is clear from the descriptions of the Examples, even when the PBS is suitably diluted or its pH value is adjusted, the peptide can also be bonded to a silicon nitride substrate.

The "silicon nitride substrate" is not limited, as long as it comprises silicon nitride without surface modification on a part of or the entire surface of the substrate, and a peptide having an affinity for silicon nitride can be bonded to the surface of the silicon nitride. Examples of the silicon nitride substrate include a substrate formed of silicon nitride, and a substrate comprising a component/components other than silicon nitride wherein silicon nitride is deposited or covers a part of or the entire surface thereof.

The peptide having an affinity for silicon nitride of the present invention can be prepared by employing a known genetic engineering technique or chemosynthesis method. For example, a desired peptide may be prepared by inserting a polynucleotide encoding peptide represented by any one of SEQ ID NOS: 1 to 11 and 23 to 35 into a vector or the like, and then culturing a transformant comprising the vector included therein. The peptide having an affinity for silicon nitride of the present invention may be obtained by isolating and/or purifying the peptide from a microorganism that is capable of producing the peptide of the present invention. The peptide having an affinity for silicon nitride of the present invention may also be synthesized by a known chemosynthesis method based on the information of the amino acid sequence represented by any one of SEQ ID NOS: 1 to 11 and 23 to 35 or the nucleotide sequence encoding the amino acid sequence. The chemosynthesis method encompasses a peptide synthesis method, such as liquid-phase peptide synthesis and solid-phase peptide synthesis. The determination of whether the obtained peptide has an affinity for silicon nitride may be performed, in the same manner as described above, based on whether the obtained peptide can directly bond to a silicon nitride substrate without surface modification. If the peptide can directly bond to the silicon nitride, it can be concluded that such a peptide has an affinity. As described above, the bonding conditions may be suitably selected depending on the types of the peptide used, depending on the target protein to be immobilized to the silicon nitride substrate via the peptide, or depending on the properties of the desired substance having an interaction with the target protein.

Because the peptide of the present invention has an affinity for silicon nitride, the target protein can thereby be immobilized to a silicon nitride substrate easily and in a highly dense manner via the peptide having an affinity for silicon nitride. The peptide having an affinity for silicon nitride of the present invention also allows the target protein to be immobilized to a silicon nitride substrate while sufficiently maintaining the activity thereof, and further allows the target protein to be immobilized to a silicon nitride substrate while controlling the uniformity of the target protein orientation. This indicates that the present invention allows the target protein to be immobilized to a silicon nitride substrate via a peptide having an affinity for silicon nitride in a highly accurate and efficient manner. Furthermore, the present invention allows a substance having an interaction with the target protein to bond to a silicon nitride substrate via the peptide having an affinity for silicon nitride in a highly accurate and efficient manner.

Therefore, the peptide having an affinity for silicon nitride of the present invention may be suitably used in the preparation of biochips, including a protein chip, column packing materials, microplates for use in ELISA, and immobilized enzymes.

As described above, the peptide having an affinity for silicon nitride of the present invention is very useful for immobilizing a target protein to a silicon nitride substrate.

This indicates that the present invention provides a linker for immobilizing a target protein to a silicon nitride substrate, wherein the linker comprises a peptide having an affinity for silicon nitride; a composition for immobilizing the target protein to the silicon nitride substrate, the composition comprising the peptide having an affinity for silicon nitride; and the use of a peptide having an affinity for silicon nitride for immobilizing the target protein to a silicon nitride substrate. In the linker, the composition and use of a peptide having an affinity for silicon nitride according to the present invention, the peptide having an affinity for silicon nitride, the silicon nitride substrate, the target protein, the immobilizing (bonding) conditions, etc., and the effects obtained therefrom are the same as those explained above. As described above, the linker can immobilize the target protein to a silicon nitride substrate via a peptide having an affinity for silicon nitride. The composition for immobilizing the target protein to the silicon nitride substrate, wherein the composition comprises a peptide having an affinity for silicon nitride, is not limited as long as it comprises a peptide having an affinity for silicon nitride, and it may further comprise components necessary for immobilizing the target protein to a silicon nitride substrate via a peptide having an affinity for silicon nitride, such as an arbitrary solution including a buffer, e.g., PBS, that allows a peptide having an affinity for silicon nitride to bond to a silicon nitride substrate, a target protein, and/or a silicon nitride substrate. The use of such a composition makes it possible to easily bond the peptide having an affinity for silicon nitride to a silicon nitride substrate. This allows the target protein to be readily immobilized to a silicon nitride substrate via a peptide having an affinity for silicon nitride.

In this specification, the term "comprising" also encompasses the meanings "consisting essentially of" and "consisting of."

2. Polynucleotide

The present invention further provides a polynucleotide encoding a peptide having an affinity for silicon nitride. The polynucleotide of the present invention is not limited as long as it encodes the peptide having an affinity for silicon nitride described above, and the examples of the polynucleotide include the following:

(2-1) a polynucleotide encoding a peptide having an affinity for silicon nitride, (2-2) a polynucleotide comprising a nucleotide sequence represented by any one of SEQ ID NOS: 12 to 22 and 36 to 48, and (2-3) a polynucleotide hybridizing to a complementary strand of either the polynucleotide of (2-1) or (2-2) under stringent conditions and encoding a peptide having an affinity for silicon nitride.

Here, a person having ordinary skill in the art can readily analyze and obtain the polynucleotide of (2-1) described above by a known method based on the amino acid sequence of a peptide having an affinity for silicon nitride.

The amino acid sequence encoded by each polynucleotide of (2-2) respectively corresponds to the amino acid sequence represented by SEQ ID NOS: 1 to 11 and 23 to 35.

In (2-3) described above, the expression "hybridizing . . . under stringent conditions" indicates that two polynucleotide fragments can hybridize to each other under standard hybridization conditions. The conditions are disclosed in Sambrook et al., Molecular Cloning: A laboratory manual (1989), Cold Spring Harbor Laboratory Press, New York, USA. More specifically, "stringent conditions" as used herein refers to hybridization in 6.0×SSC at about 45° C., followed by washing with 2.0×SSC at 50° C.

A polynucleotide that hybridizes to a complementary strand under stringent conditions generally has a certain degree or more of identity to any one of the nucleotide sequences of (2-1) and (2-2) described above. The polynucleotide has, for example, 70% or more, preferably 85% or more, more preferably 90% or more, further more preferably 95% or more, particularly preferably 98% or more, and yet more particularly preferably 99% or more identity to the nucleotide sequence mentioned above. The identity of the nucleotide sequence can be determined using a commercially available analytical tool or an analytical tool available through telecommunication (e.g., internet). For example, software, such as FASTA, BLAST, PSI-BLAST, or SSEARCH, can be used for the calculation.

The term "having an affinity for silicon nitride" means the same as that explained above and is not particularly limited as long as the peptide prepared using the polynucleotide and a silicon nitride without surface modification can be directly bonded, and a person having ordinary skill in the art can suitably select the bonding conditions as described above. Preparation of a peptide from the polynucleotide may be performed using a genetic engineering technique or a chemosynthesis method known in this field, which is easy for a person skilled in the art. For example, a peptide may be prepared by using, for example, an expression vector described below.

The polynucleotide of the present invention can also be prepared by a known genetic engineering technique or chemosynthesis method (see Proc. Natl. Acad. Sci., USA., 78, 6613 (1981); Science, 222, 778 (1983); Molecular Cloning 2d Ed, Cold Spring Harbor Lab. Press (1989); Lectures on Biochemical Experiments (Genetic Research Methods I, II, III), Journal of The Japanese Biochemistry Society (1986). For example, the polynucleotide may be obtained by preparing a cDNA library from a suitable source, such as microorganisms comprising the desired polynucleotide, using a standard method, followed by obtaining the desired polynucleotide using a suitable probe or the like from the library. Alternatively, the polynucleotide of the present invention may be easily prepared and/or obtained by a known chemical DNA synthetic process based on the sequence information of the amino acid represented by any one of SEQ ID NOS: 1 to 11 and 23 to 35 or the sequence information of the nucleotide represented by any one of SEQ ID NOS: 12 to 22 and 36 to 48.

3. Expression Vector

The present invention provides an expression vector comprising the aforementioned polynucleotide for expressing a peptide having an affinity for silicon nitride. The expression vector for expressing a peptide having an affinity for silicon nitride of the present invention is not particularly limited as long as it comprises the polynucleotide and can express in the host cell, based on the base sequence of the polynucleotide, a peptide having an affinity for silicon nitride or a linker for immobilizing a target protein to a silicon nitride substrate, the linker comprising a peptide having an affinity for silicon nitride. As conventionally known, a vector is generally suitably selected based on the relationship with the host cell.

More specifically, the vector used in the present invention is not limited as long as it is an expression vector generally used in the genetic engineering field. Examples thereof include plasmid vectors, such as pBR, pUC, pCD, pET, pGEX, pCMV, pMSG, and pSVL derived from bacteria such as *E. coli* or yeast; and viral vectors derived from retrovirus, adenovirus, vacciniavirus, baculovirus, bacteriophage, etc. As described above, these vectors may be suitably selected depending on the relationship with the host cell.

A promoter is linked to these vectors if necessary. The promoter is not limited as long as it is suitable for the host cell, and any known promoter can be used. Examples of the promoter include lac promoter, trp promoter, tac promoter, trc promoter, racA promoter, λPL promoter, lpp promoter, and T7 promoter, and these promoters are used, for example, when *E. coli* is used as the host cell. Other examples of the promoter include SV40 promoter, CMV promoter, RSV promoter, HSV-TK promoter, LTR promoter, SRα promoter, and EF-1α promoter. These promoters are used when animal cells are used as the host cells. In view of the relationship with the host cell, the following promoters may also be used: yeast cell promoters, insect cell promoters, and viral promoters. When a vector has an endogenous promoter therein, the endogenous promoter may also be used.

The promoter-bonding site in the expression vector for expressing a peptide having an affinity for silicon nitride of the present invention is not limited, as long as the peptide having an affinity for silicon nitride can be expressed in the host cell. Generally, the promoter is linked to a site upstream in the base sequence of a polynucleotide encoding the peptide having an affinity for silicon nitride. More specifically, in the expression vector for expressing a peptide having an affinity for silicon nitride of the present invention, the polynucleotide encoding the peptide having an affinity for silicon nitride is under the control of the promoter.

As the host cell, various known prokaryotic cells and eukaryotic cells may be used. Examples thereof include bacteria, such as *E. coli, Bacillus subtilis, Streptococcus, Staphylococcus*, actinomycetes, and filamentous fungi; cells, such as yeast, *Aspergillus*, insect cells including *Drosophila* S2, and *Spodoptera* Sf9; animal or plant cells, such as L cells, CHO cells, COS cells, Art-20 cells, HeLa cells, C127 cells, myeloma cells, GH3 cells, FL cells, VERO cells, CV-1 cells, Bowes melanoma cells, and oocytes of platanna.

These vectors, promoters and host cells may be suitably combined based on the common general technical knowledge in this field. Examples of combinations include pET (T7 promoter)/*E. coli* BL21 (DE3), and pGEX (Tac promoter)/*E. coli* BL21.

In the expression vector for expressing a peptide having an affinity for silicon nitride of the present invention, base sequences of an enhancer, splicing signal, poly-A additional signal, drug resistance gene, Green Fluorescent Protein (GFP) or other marker genes, may further be comprised. These base sequences may be linked at any site of the expression vector, depending on a purpose.

A base sequence constituting the linker for inserting a peptide having an affinity for silicon nitride into the target protein may be further connected to the expression vector for expressing a peptide having an affinity for silicon nitride of the present invention. For example, the base sequence constituting the linker may be connected to the 5' terminal and/or 3' terminal of the polynucleotide that encodes a peptide having an affinity for silicon nitride. The base sequence constituting the linker is not limited as long as the effects of the present invention can be achieved, and a person skilled in the art may suitably select within the general scope of investigation using a known technique. Examples of the linker include so-called flexible linkers, and an example of the amino acid sequence of a widely used flexible linker is such that $(G4S)_n$ (for example, n=1 to 4). When the linker is used, a nucleotide sequence capable of suitably expressing the linker may be connected to the linker.

Furthermore, in the expression vector for expressing the peptide having an affinity for silicon nitride of the present invention, a polynucleotide encoding a target protein may further be linked to a polynucleotide that encodes a peptide having an affinity for silicon nitride. By linking the polynucleotide encoding the target protein to a polynucleotide encoding the peptide having an affinity for silicon nitride, the target protein linked by a peptide having an affinity for silicon nitride can be expressed. This also enables to express the target protein linked by a linker for immobilizing the target protein to a silicon nitride substrate. Expression vectors comprising a polynucleotide encoding the target protein and a peptide having an affinity for silicon nitride, or comprising a polynucleotide encoding the target protein and a linker for immobilizing the target protein to a silicon nitride substrate may be referred to as an expression vector for expressing a peptide fusion protein that comprises a peptide having an affinity for silicon nitride and a target protein.

Here, the target protein is not particularly limited and includes any protein, such as an antigen, antibody, enzyme, biological substrate, receptor protein, and lectin. More specifically, although not limited to these, examples thereof include glutathione transferase (GST: G lutathione S-Transferase), GFP (green fluorescent protein), alkaline phosphatase, peroxidase, luciferase, β-galactosidase, trypsin, chymotrypsin, thrombin, Factor Xa, angiotensin conversion enzyme, tyrosine kinase, insulin receptor, EGF receptor, maltose-bonding protein, monoclonal antibody, polyclonal antibody, single-chain antibody, multivalent single-chain antibody (e.g., bivalent single-chain antibody), constant region fusion single-chain antibody, Fab fragment and F(ab')2 fragment (fragments of antibodies including antigen-bonding sites), complement system protein C1q, concanavalin A, lentil lectin, antibody-bonding protein (e.g., protein A, ZZ, protein G, and protein L), biotin, and streptavidin (avidin).

When the base sequences of nucleotides encoding these target proteins are known, based on the already known sequence information of the nucleotide encoding the target protein, a desired nucleotide sequence may be positioned on the expression vector by a known method. When the base sequence of the nucleotide encoding the target protein is unknown, a known genetic engineering technique or a chemosynthesis method may be employed to analyze and prepare the nucleotide encoding the target protein based on the amino acid sequence of the target protein, and the resulting nucleotide may be positioned on the expression vector.

In order to express the peptide fusion protein, the polynucleotide encoding the target protein is positioned under the control of the promoter in the same manner as the polynucleotide encoding peptide having an affinity for silicon nitride. As far as the above is met, a person skilled in the art may suitably select whether the polynucleotide encoding the target protein is to be linked upstream or downstream of the polynucleotide encoding the peptide having an affinity for silicon nitride, and whether the polynucleotide encoding the peptide having an affinity for silicon nitride is linked to the interior molecule of the target protein. In either case, the polynucleotide is preferably linked to a site that does not adversely affect the physiological activity and conformation of the target protein. For example, when the target protein is an antigen, the polynucleotide is preferably positioned on a site that does not adversely affect antigen determination; when the target protein is an antibody, the polynucleotide may be positioned on a site that does not adversely affect antigen-bonding; and when the target protein is an enzyme, the polynucleotide may be positioned on a site that does not adversely affect enzyme activity; etc. A person skilled in the art may suitably select the introduction site depending on the properties and structures of the target proteins, such as antigen, antibody, enzyme, biological substrate, receptor protein, and lectin. In any case, the peptide having an affinity for silicon nitride or the linker for immobilization is preferably linked to a site that does not affect the properties of the peptide having an affinity for silicon nitride, such as an affinity for a substrate, and that does not adversely affect the effects of the present invention.

In the expression vector for expressing a peptide fusion protein of the present invention, a polynucleotide encoding the peptide having an affinity for silicon nitride is linked to the polynucleotide encoding the target protein, and the linkage structure is not limited as long as a desired peptide fusion protein is expressed in the host cell. For example, in the peptide fusion protein expression vector of the present invention, a polynucleotide encoding a peptide having an affinity for silicon nitride and a polynucleotide encoding a target protein may be present as a continuous base sequence. More specifically, the polynucleotide encoding the target protein may be directly linked without a linker, or the polynucleotide encoding the target protein may be linked to the polynucleotide encoding peptide having an affinity for silicon nitride through some sequence, such as a base sequence that is capable of linking these polynucleotides.

A linker for linking a polynucleotide encoding the peptide having an affinity for silicon nitride to the polynucleotide encoding the target protein is not limited as long as the peptide fusion protein is expressed and the effects of the present invention are achieved, and a person skilled in the art may suitably select a linker within the ordinary scope using a known technique. As one example thereof, the flexible linker described above can be mentioned.

These expression vectors of the present invention may be prepared using a known method in this field, by positioning necessary base sequences, such as a polynucleotide encoding a peptide having an affinity for silicon nitride or a polynucleotide encoding a target protein, on a suitable site of the vector using a restriction enzyme or the like.

4. Transformant

The present invention provides a transformant obtained by transforming a host cell by introducing the expression vector thereinto.

In the present invention, examples of the host cell include those described above.

The method for obtaining a transformant by introducing a peptide fusion protein expression vector into the host cell is not particularly limited and a generally known method may be employed. For example, the transformant may be formed by various methods described in standard laboratory manuals. Specific examples thereof include a calcium chloride method, a rubidium chloride method, transfection using a DEAE-dextran, microinjection, cationic lipid-mediated transfection using, for example, a liposome, electroporation, transduction, and infection by bacteriophage.

5. Peptide Fusion Protein

The present invention provides a peptide fusion protein comprising a peptide having an affinity for silicon nitride and a target protein, wherein the peptide fusion protein can be obtained from the transformant described above.

The transformant, peptide having an affinity for silicon nitride, and target protein are the same as those described above. In the present invention, the peptide fusion protein is a fusion protein unified by linking a peptide having an affinity for silicon nitride to a target protein as described above.

In the present invention, the peptide fusion protein can be prepared by culturing the transformant in a suitable culture medium, and collecting the desired peptide fusion protein from the transformant and/or culture.

The culturing and collection methods are not particularly limited, and conventionally known general methods may be employed. For example, culturing may be performed by passage culture or batch culture using any culture medium suitable for the host cell. The culturing may be continued until the adequate amount of peptide fusion protein can be obtained using the amount of the protein produced inside and outside of the transformant as an index. The culture medium used in the aforesaid culturing may be suitably selected from various commonly used culture media depending on the host cell. The culture conditions, such as temperature and time, may also be suitably selected from known conditions depending on the host cell.

The peptide fusion protein thus obtained may be further isolated or purified, if necessary, by various isolation operations utilizing its physical properties, chemical properties or the like. Examples of the isolation operations include solvent extraction, distillation, and various types of chromatography (see Biochemistry Data Book II), pp. 1175-1259, First Edition, First Printing, 1980, Kagaku-Dojin Publishing Co., Inc., Tokyo; Biochemistry, 25(25), 8274 (1986); Eur. J. Biochem., 163, 313 (1987)). The peptide fusion protein of the present invention has an affinity for silicon nitride. Therefore, the peptide fusion protein may be isolated and purified by contacting the product obtained from a culture medium or transformant with a silicon nitride substrate to bond the peptide having an affinity for silicon nitride to the silicon nitride substrate. When the protein is expressed using a transformant, a peptide fusion protein may sometimes be present as an inclusion body. In this case, the peptide fusion protein of the present invention may be isolated or purified by suitably solubilizing the inclusion body and contacting it with a silicon nitride substrate to bond a peptide having an affinity for silicon nitride to the silicon nitride substrate so as to isolate and purify the peptide fusion protein of the present invention. When the conformation of the peptide fusion protein of the present invention has been changed, the peptide fusion protein may be bonded to the silicon nitride substrate with the conformational change being maintained, and the conformation may also be refolded, if necessary, while being bonded, to isolate or purify the peptide fusion protein of the present invention.

6. Silicon Nitride Substrate to which a Peptide Having an Affinity for Silicon Nitride has been Bonded The present invention provides a silicon nitride substrate to which a peptide having an affinity for silicon nitride has been bonded. It comprises a peptide having an affinity for silicon nitride bonded to the silicon nitride substrate. The peptide having an affinity for silicon nitride is the same as described above.

In the present invention, the silicon nitride substrate is the same as that described above. The silicon nitride substrate of the present invention is not limited, as long as it comprises silicon nitride without surface modification on a part and/or the entire surface of the substrate, and the peptide having an affinity for silicon nitride can be bonded to the surface of the silicon nitride. Examples of the silicon nitride substrate include a substrate formed of silicon nitride, and a substrate comprising a component/components other than silicon nitride wherein silicon nitride is deposited or covers a part of or the entire surface thereof.

The shape of the silicon nitride substrate is not limited as long as the peptide having an affinity for silicon nitride can be bonded thereto, and the silicon nitride substrate may be in any shape, such as a plate shape, film shape (sheet), spherical, granular (bead shape), fibrous, microplate, or cylindrical. When the silicon nitride substrate of the present invention is used as a biochip, such as a protein chip, the silicon nitride substrate is preferably, for example, in the shape of a plate, film (sheet) or the like.

The silicon nitride substrate to which a peptide having an affinity for silicon nitride has been bonded can be prepared by contacting the peptide having an affinity for silicon nitride or a linker for immobilizing the target protein to a silicon nitride substrate comprising the peptide having an affinity for silicon nitride so as to bond the peptide having an affinity for silicon nitride to a silicon nitride substrate. The bonding conditions may be suitably selected depending on the type of peptide having an affinity for silicon nitride, the properties of the target protein to be immobilized to the silicon nitride substrate via the peptide or depending on the properties of the desired substance having an interaction with the target protein. For example, the silicon nitride substrate can be prepared by a method such as dripping a solution obtained by mixing the peptide having an affinity for silicon nitride with an optional solvent/solvents, or a composition for immobilizing the target protein to the silicon nitride substrate, the composition comprising a peptide having an affinity for silicon nitride, onto a silicon nitride substrate; or by a method such as immersing a silicon nitride substrate in the solution, and then allowing the result to stand for a certain period of time. In order to remove unnecessary components unbonded to the silicon nitride substrate, the unnecessary components may be, for example, washed off using a solvent, such as a buffer solution or water. The bonding conditions of the Examples described latter may be employed, and a person skilled in the art may suitably select the bonding conditions with reference to those described in the Examples.

Because the peptide has an affinity for silicon nitride, direct bonding thereof to a silicon nitride substrate is possible in the present invention.

The silicon nitride substrate to which a peptide having an affinity for silicon nitride has been bonded of the present invention may further comprise a target protein immobilized to the silicon nitride substrate via the peptide having an affinity for silicon nitride. The target protein is the same as those described above.

The immobilization is not limited, as long as the target protein is immobilized to a silicon nitride substrate via a peptide having an affinity for silicon nitride. The target protein may be immobilized to a silicon nitride substrate via a peptide having an affinity for silicon nitride by introducing the peptide having an affinity for silicon nitride to the target protein and contacting the result to a silicon nitride substrate. Alternatively, the target protein may be immobilized to a silicon nitride substrate via a peptide having an affinity for silicon nitride by introducing a peptide having an affinity for silicon nitride bonded to a silicon nitride substrate into the target protein. Such contact makes it possible to prepare a silicon nitride substrate comprising the target protein immobilized thereto via a peptide having an affinity for silicon nitride. The contacting conditions for the silicon nitride substrate are the same as those described above.

Introduction of a peptide having an affinity for silicon nitride to the target protein is not limited, as long as it does not adversely affect the effects of the present invention and as long as the peptide having an affinity for silicon nitride can be introduced. The peptide having an affinity for silicon nitride may be introduced to the target protein directly or via a linker. In the same manner as described above, a person skilled in the art may suitably select the linker based on known common general technical knowledge insofar as it does not adversely affect the effects of the present invention.

The introduction site of the peptide having an affinity for silicon nitride to the target protein is not limited as long as it does not adversely affect the activity and orientation of the target protein, the affinity and other properties of the peptide having an affinity for silicon nitride relative to the substrate, and the effects of the present invention; the peptide having an affinity for silicon nitride can be introduced into any site. For example, when the target protein is an antigen, the peptide having an affinity for silicon nitride may be positioned on a site that does not adversely affect the antigen determination; when the target protein is an antibody, the peptide having an affinity for silicon nitride may be positioned on a site that does not adversely affect the antigen-bonding; and when the target protein is an enzyme, the peptide having an affinity for silicon nitride may be positioned on a site that does not adversely affect the enzyme activity; etc. A person skilled in the art may suitably select the site depending on the properties and structures of the target proteins, such as an antigen, antibody, enzyme, biological substrate, receptor protein, or lectin. In particular, the introduction site of the peptide having an affinity for silicon nitride can be suitably selected in the present invention; this allows the target protein to be immobilized to a silicon nitride substrate while sufficiently maintaining target protein activity, and while also uniformly controlling target protein orientation.

The method for introducing a peptide having an affinity for silicon nitride into the target protein is not particularly limited, and the peptide may be introduced by a suitably selected known genetic engineering technique or chemosynthesis method. For example, the peptide may be introduced by utilizing an expression vector as described above.

Furthermore, the peptide having an affinity for silicon nitride may be introduced into the target protein using a cross linking agent, including glutaraldehyde, NHS/EDC (N-hydroxysuccinimide/1-ethyl-3-(3-dimethylaminopropyl)carbodiimide hydrochloride) or the like. Alternatively, a peptide having an affinity for silicon nitride may be introduced into the target protein by a specific bonding between a biotinized peptide having an affinity for silicon nitride and a streptavidin (avidin)-labeled target protein via biotin-streptavidin (avidin). Furthermore, a peptide having an affinity for silicon nitride may also be introduced into the target protein by a specific bonding between a biotinized peptide having an affinity for silicon nitride and a biotinized target protein via biotin-streptavidin (avidin). The introduction may be performed by a known method as described above.

A preferable example for introducing a peptide having an affinity for silicon nitride into a target protein is the use of a peptide fusion protein. By contacting a peptide fusion protein with the silicon nitride substrate as described above, the target protein can be immobilized to a silicon nitride substrate via a peptide having an affinity for silicon nitride. Alternatively, the target protein can also be immobilized to a silicon nitride substrate via a peptide having an affinity for silicon nitride by introducing a peptide having an affinity for silicon nitride into the target protein using a cross linking agent or specific bonding, and then contacting the result with a silicon nitride substrate as described above. This indicates that the present invention provides a method for producing a target protein capable of immobilizeding to a silicon nitride substrate, the method comprising introducing a peptide having an affinity for silicon nitride into the target protein, or provides a target protein comprising a peptide having an affinity for silicon nitride introduced thereinto.

The target protein can also be immobilized to a silicon nitride substrate via a peptide having an affinity for silicon nitride by introducing a peptide having an affinity for silicon nitride bonded to the silicon nitride substrate into the target protein using the aforementioned cross linking agent, specific bonding, or the like.

The silicon nitride substrate to which a peptide having an affinity for silicon nitride has been bonded of the present invention allows the target protein to be immobilized to a silicon nitride substrate in a highly dense manner while sufficiently maintaining target protein activity, and while also uniformly controlling target protein orientation. Therefore, the silicon nitride substrate to which a peptide having an affinity for silicon nitride has been bonded of the present invention allows the target protein and/or a substance having an interaction with the target protein to be detected, measured, analyzed, etc., in a highly accurate and efficient manner.

Therefore, when the silicon nitride substrate to which a peptide having an affinity for silicon nitride has been bonded according to the present invention is in the shape of a plate, film (sheet) or the like, it can be used as a biochip, in particular, as a protein chip. The silicon nitride substrate to which a peptide having an affinity for silicon nitride has been bonded according to the present invention is suitably used as a column packing material utilizing an antigen-antibody reaction, enzyme reaction or the like, microplates for use in ELISA or the like, and immobilized enzymes. The substrate of the present invention is useful in various fields, such as clinical examination, drug discovery research, environmental monitoring, and biochemistry.

7. Method for Immobilizing a Target Protein to a Silicon Nitride Substrate

The present invention provides a method for immobilizing a target protein to a silicon nitride substrate, the method comprising a step of contacting a peptide having an affinity for silicon nitride introduced into the target protein to a silicon nitride substrate.

Here, the target protein, peptide having an affinity for silicon nitride, silicon nitride substrate, introduction of a peptide having an affinity for silicon nitride into the target protein, and contacting the peptide having an affinity for silicon nitride introduced into the target protein to a silicon nitride substrate, are the same as those described above.

According to the immobilization method of the present invention, because the peptide has an affinity for silicon nitride, bonding thereof to the silicon nitride substrate is possible by simply contacting the peptide having an affinity for silicon nitride introduced into the target protein with a silicon nitride substrate. Therefore, the immobilization method of the present invention makes it possible that a target protein is easily immobilized to the silicon nitride substrate via the peptide has an affinity for silicon nitride.

The immobilization method of the present invention may be performed by further combining a step of introducing a peptide having an affinity for silicon nitride into the target protein. More specifically, the method can be performed after conducting the step of introducing the peptide having an affinity for silicon nitride into the target protein.

The step of introducing the peptide having an affinity for silicon nitride into the target protein is not limited as long as it does not adversely affect the effects of the present invention and the peptide having an affinity for silicon nitride can be introduced. The introduction may be suitably performed by employing a known genetic engineering technique or chemosynthesis method, for example, by utilizing an expression vector. As one example, the introduction may be performed in accordance with the procedure of expressing the peptide fusion protein described above. Therefore, in introducing a peptide having an affinity for silicon nitride into a target protein, the use of the expression vector or transformant described above can also be mentioned as a preferable example. In the same manner as described above, the use of a cross linking agent, specific bonding between biotin and streptavidin (avidin), or the like can also be mentioned as a preferable example for introducing a peptide having an affinity for silicon nitride into the target protein. Furthermore, in the same manner as described above, the introduction site is not limited as long as the peptide having an affinity for silicon nitride can be introduced into the target protein directly or via a linker, and a person skilled in the art can suitably select the introduction site depending on the properties and structure of the target protein.

According to the immobilization method of the present invention described above, a silicon nitride substrate comprising a target protein immobilized thereto can be easily prepared. Furthermore, in the immobilization method of the present invention, because the target protein is immobilized to the silicon nitride substrate via a peptide having an affinity for silicon nitride, the target protein can be immobilized in a highly dense manner while sufficiently maintaining target protein activity, and while also uniformly controlling target protein orientation. The immobilization method of the present invention allows a silicon nitride substrate comprising the target protein immobilized thereto via a peptide having an affinity for silicon nitride to be easily prepared. This also allows the preparation of a biochip, such as a protein chip, as well as column packing materials utilizing an antigen-antibody reaction, enzyme reaction, or the like, microplates for use in ELISA, and immobilized enzymes. This indicates that the immobilization method of the present invention is useful in various fields, such as clinical examinations, drug discovery, environmental monitoring, and biochemistry.

Further, the present invention provides a method for immobilizing a target protein to a silicon nitride substrate, the method comprising bonding the target protein to a peptide having an affinity for silicon nitride contained in a silicon nitride substrate to which a peptide having an affinity for silicon nitride has been bonded.

Here, the target protein, the peptide having an affinity for silicon nitride, and the silicon nitride substrate are the same as described above. Bonding a peptide having an affinity for silicon nitride to a silicon nitride substrate is also the same as described above.

In the present invention, bonding the peptide having an affinity for silicon nitride bonded to a silicon nitride substrate to the target protein is not limited as long as it does not adversely affect the effects of the present invention, and as long as they can be bonded; a person skilled in the art may suitably select the method based on known common general technical knowledge. For example, by introducing a peptide having an affinity for silicon nitride bonded to a silicon nitride substrate into the target protein, using a cross linking agent or specific bonding, the target protein may be immobilized to a silicon nitride substrate via a peptide having an affinity for silicon nitride. As described above, the bonding is not limited as long as the peptide having an affinity for silicon nitride is bonded to the target protein directly or via a linker, and as described above, a person skilled in the art may suitably select the linker based on known common general technical knowledge within the range that does not adversely affect the effects of the present invention. The bonding site through which the peptide having an affinity for silicon nitride is bonded to the target protein is not limited as long as the effects of the present invention are not adversely affected, and a person skilled in the art may suitably select the bonding site depending on the properties and structure of the target protein as described above.

The immobilization method of the present invention may be performed by further combining a step of contacting the peptide having an affinity for silicon nitride to a silicon nitride substrate. More specifically, it can be performed after conducting the step of contacting the peptide having an affinity for silicon nitride to a silicon nitride substrate. Contacting the peptide having an affinity for silicon nitride to a silicon nitride substrate may be performed as described above.

According to the immobilization method of the present invention, as described above, a silicon nitride substrate comprising the target protein immobilized thereto can be prepared. Because the target protein is immobilized to the silicon nitride substrate via a peptide having an affinity for silicon nitride, the target protein can be immobilized in a highly dense manner while sufficiently maintaining target protein activity, and while also uniformly controlling target protein orientation. Accordingly, the present invention eases the preparation of a biochip, including a protein chip, column packing materials utilizing an antigen-antibody reaction, an enzyme reaction or the like, microplates for use in ELISA or the like, and immobilized enzymes. This indicates that the immobilization method of the present invention is useful in various fields, such as clinical examinations, drug discovery research, environmental monitoring, and biochemistry.

EXAMPLE

In the following, the present invention will be described with reference to Examples but is not limited to the following Examples.

Example 1

The affinity of the polypeptide (SIN1 peptide) represented by SEQ ID NO: 1 and that of the polypeptide (SIN2 peptide) represented by SEQ ID NO: 2 for a silicon nitride ($Si_3N_4$) substrate were examined in accordance with the procedure described below.

1. Procedure

Construction of Elongation Factor Tu (ELN) Expression Vector

1) Chromosomal DNA of *E. coli* BL21(DE3) (Novagen) was extracted using a DNA Purification Kit (manufactured by Promega KK).
2) PCR was conducted with the chromosomal DNA as a template using KOD plus ver. 2 PCR kit (manufactured by Toyobo Co., Ltd.) to amplify the ELN gene.
3) The amplified ELN gene was inserted between the Nde I site and the Not I site of a pET-22(b) vector (manufactured by Novagen) using an In-Fusion (registered trademark) Advantage PCR Cloning Kit (manufactured by Clontech Laboratories, Inc.) and was then cloned.
4) *E. coli* HST08 Premium (TAKARA BIO INC.) was transformed with the above vector and was statically cultured overnight on an LB-Amp agar medium.
5) 1 mL of Amp.-containing Plusgrow (manufactured by Nacalai Tesque, Inc.) was put into a 1.5-mL tube, inoculated with a colony from the agar plate, and cultured at 37° C. and 200 rpm for about 7 hours.
6) After the culturing, the vector was collected and purified by an alkali SDS method.
7) Insertion of the gene was confirmed by agarose electrophoresis, and further the nucleotide sequence of the inserted ELN gene was confirmed by DNA sequence analysis.
8) *E. coli* 1M109 (TAKARA BIO INC.) was transformed with the vector obtained in the above step 6) and cultured, and then an ELN expression vector was collected and purified.

Construction of GST Expression Vector pGEX-3X 1) 1 µL of a GST expression vector (pGEX-3X) (manufactured by GE Healthcare) was added to 500 µL of *E. coli* 1M109 competent cells, and the mixture was incubated on ice for 10 minutes.
2) The mixture was incubated at 42° C. for 45 seconds and was cooled on ice.
3) 10 mL of Amp.-containing Plusgrow was put into a 15-mL tube, and 500 µL of the above transformed *E. coli* was added thereto, and the mixture was cultured at 37° C. and 200 rpm overnight.
4) Centrifugal separation was conducted at 4,500 rpm for 15 minutes, and the supernatant was removed.
5) pGEX-3X was collected by an alkali lysis method.
6) 25 µL of NEBuffer (manufactured by New England Biolabs, Inc.), 2.5 µL of ×100 BSA (manufactured by New England Biolabs, Inc.), 2.5 µL of CIAP (Calf Intestine Alkaline Phosphatase, manufactured by Toyobo Co., Ltd.), 2.5 µL of Eco RI-HF (manufactured by New England Biolabs, Inc.), and 2.5 µL of Bam HI-HF (manufactured by New England Biolabs, Inc.) were added to 215 µL of the collected vector solution, and the mixture was incubated at 37° C. overnight to conduct cleavage/dephosphorylation treatment of the vector. The cleavage state of pGEX-3X was confirmed by agarose electrophoresis.

7) The enzymically-treated vector was purified using a PCR Clean-Up System (manufactured by Promega KK).

Preparation of GST (Glutathione-S-Transferase) Fused with SIN1 Peptide or SIN2 Peptide 1) Each of the nucleotide sequences encoding the SIN1 peptide and SIN2 peptide was amplified using the aforementioned ELN expression vector as a template. The nucleotide sequence encoding the SIN1 peptide is represented by SEQ ID NO: 12, and the nucleotide sequence encoding the SIN2 peptide is represented by SEQ ID NO: 13.

2) Each of the nucleotide sequences obtained in the above step 1) was cloned between the Bam HI site and the Eco RI site of the GST expression vector pGEX-3X constructed as described above, and each of the nucleotide sequences encoding the SIN1 peptide and SIN2 peptide, which had been inserted into the vector, was confirmed by DNA sequence analysis.

3) E. coli BL21(DE3) was transformed with the constructed expression vector and was cultured overnight in 10 mL of a 2×YT medium (manufactured by Novagen) containing ampicillin (Amp., manufactured by Nacalai Tesque, Inc.).

4) The cultured medium was added to 50 mL of the same medium as in the above step 3) until OD600=0.1, and the mixture was cultured at 37° C. and 200 rpm until OD600=1.0 was obtained (about 2 hours).

5) 5 µL of 1M IPTG (Isopropyl-β-DH-thiogalactopyranoside, manufactured by Wako Pure Chemical Industries, Ltd.) was added, and the mixture was further cultured at 30° C. and 200 rpm for 7 hours.

6) After the culturing, centrifugal separation was conducted at 4,500 rpm for 20 minutes, and the supernatant was removed.

7) 3 mL of BugBuster (BugBuster Protein Extraction Reagent, manufactured by Novagen), 1.5 µL of Benzonase Nuclease (manufactured by Novagen), and 3 mg of Lysozyme (manufactured by Seikagaku Corporation) were added to the bacterial cells and the mixture was agitated well and incubated at 37° C. for 1 hour for the lysis of the bacterial cells.

8) Centrifugal separation was conducted at 10,000 rpm for 20 minutes, and the supernatant was removed as a soluble fraction.

9) The soluble fraction was applied to a GSTrap HP column (manufactured by GE Healthcare), and the interior of the column was washed with PBS that contained 1 mM DTT (Dithiothreitol, manufactured by Nacalai Tesque, Inc.).

10) Wild-type GST, SIN1 peptide-fused GST, and SIN2 peptide-fused GST were collected by gradient elution with 100 mM Tris-HCl (pH 8.0) containing 20 mM reduced glutathione.

11) The eluates were dialyzed with PBS overnight, and their densities were determined by a DC Protein Assay Kit (manufactured by Bio-Rad Laboratories, Inc.).

The PBS used in Example 1 was obtained by adding ion-exchanged water to a pre-prepared 10×PBS (NaCl (80.8 g) 1.38 M, KCl (2 g) 27 mM, $Na_2HPO_4/12H_2O$ (29 g) 80 mM, $KH_2PO_4$ (2 g) 15 mM) in a measuring cylinder to obtain a total volume of 1 L and adjusting its pH to 7.4 with HCl.

Adsorption of Wild-Type GST (Wt-GST), SIN1 Peptide-Fused GST, and SIN2 Peptide-Fused GST to $Si_3N_4$ Substrate 1) GST solutions were prepared using the PBS in such a manner that wt-GST, SIN1 peptide-fused GST, or SIN2 peptide-fused GST became 50 µg/mL (1 $cm^3$), and 1 mL of each of the GST solutions and 2 g of the $Si_3N_4$ substrate (surface area: 31.2 $cm^2$, area/volume: 31.2 $cm^{-1}$) were brought into contact with each other and were incubated at 25° C. for 3 hours.

2) Each supernatant was recovered, and the GST concentration in each of the supernatants was determined by DC Protein Assay (manufactured by Bio-Rad Laboratories, Inc.).

3) The amount of adsorption was calculated based on the difference in GST concentration before and after adsorption, and the adsorption density was calculated by dividing the amount of adsorption by the contact area (31.2 $cm^2$).

The $Si_3N_4$ substrate used here was obtained by overcoating a $Si_3N_4$ layer on a silicon dioxide ($SiO_2$) substrate by thermal deposition. A publicly-known general chemical vapor deposition was used for the overcoating of the $Si_3N_4$ layer, and the $Si_3N_4$ substrate was prepared by depositing the $Si_3N_4$ film on the $SiO_2$ substrate using dichlorosilane ($SiH_2Cl_2$) and ammonia ($NH_3$). In addition, each of the SIN1 peptide-fused GST and SIN2 peptide-fused GST prepared here was peptide-fused GST obtained by fusing the SIN1 peptide or SIN2 peptide at the C-terminal region of GST.

2. Results

The results are shown in FIG. 1.

FIG. 1 shows the adsorption density to the $Si_3N_4$ substrate. As is clear from FIG. 1, with respect to wt-GST, significant improvement in the adsorption density to the $Si_3N_4$ substrate was observed for SIN1 peptide-fused GST (GST-SIN1) and SIN2 peptide-fused GST (GST-SIN2). This indicates that the introduction of the peptide represented by SEQ ID NO: 1 or 2 allowed GTS to be easily and densely immobilized to the $Si_3N_4$ substrate. Therefore, it was revealed that the peptide represented by SEQ ID NO: 1 or 2 has a good affinity for the $Si_3N_4$ substrate and is useful for immobilization of a target protein to the $Si_3N_4$ substrate. In addition, since it was possible to introduce each of the peptides to a desired position of GST and improvement in the adsorption density was observed for the peptide-fused GST obtained thus as described above, it was revealed that, with each of the peptides, sufficient maintenance of target protein activity, and uniform control of target protein orientation are also possible.

Example 2

The affinity of the peptides represented by SEQ ID NOS: 4, 5, 7, and 11 for a $Si_3N_4$ substrate were examined in accordance with the procedure described below. In the following, TP24 denotes the peptide represented by SEQ ID NO: 4, TP25 denotes the peptide represented by SEQ ID NO: 5, TP14 denotes the peptide represented by SEQ ID NO: 7, and TP19 denotes the peptide represented by SEQ ID NO: 11.

1. Procedure

1) Synthesis of the above four types of peptides (TP24, TP25, TP14, and TP19) biotinylated at the N-terminal region was performed by a commercial vendor. Each of these biotinylated peptides was dissolved in DMF so as to have a concentration of 1 mg/mL and was stored at −20° C.

2) 10 µL (10 µg (190 µmol)) of Alexa-Fluor 633-labeled streptavidin (SA) and each biotinylated peptide equivalent to 1.5 equivalence (284 µmol) were mixed, and PBS was added to the mixture to obtain a total volume of 1 mL.

3) 1 mL of the obtained liquid mixture was brought into contact with 1 g (15.6 $cm^2$) of the $Si_3N_4$ substrate and was incubated at 25° C. for 2 hours. As a control, PBS was added to SA, and the mixture was brought into contact with the $Si_3N_4$ substrate and was incubated.

4) After the incubation, each $Si_3N_4$ substrate was washed with PBS five times and was immersed in 5 mL of PBS.

5) Each $Si_3N_4$ substrate was transferred onto a microplate (Nunc #267061), and the fluorescence intensity of the surface of the substrate was measured with a microplate reader (excitation wavelength: 620 nm, fluorescence wavelength: 666 nm). 98 measurements were conducted in total for each sample in consideration of variations of signal intensity, and averages and standard deviations were obtained.

The same $Si_3N_4$ substrate and PBS as those in Example 1 were used.

2. Results

Figure 2:
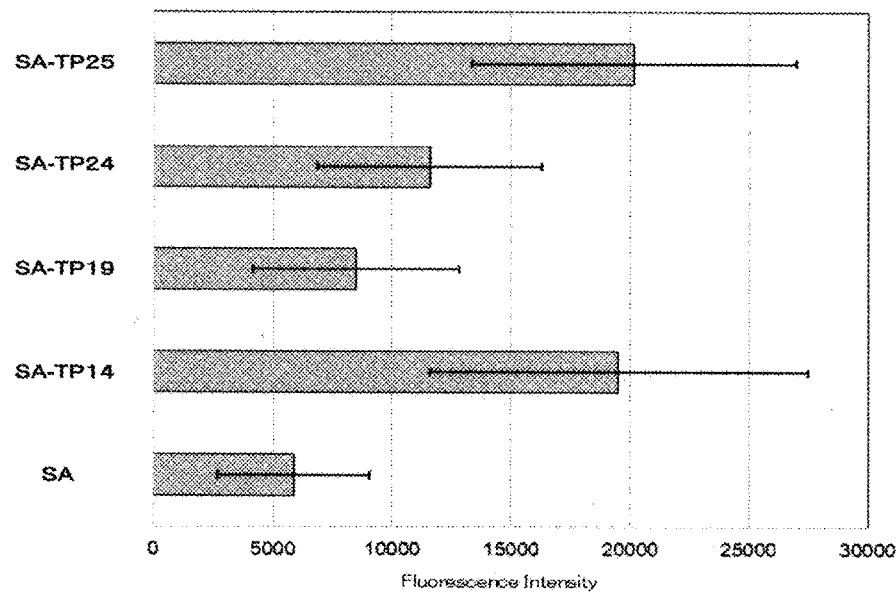
FIG. 2 indicates that the peptides represented by SEQ ID NOS: 4, 5, 7 and 11 have an affinity for a silicon nitride substrate.

The results are shown in FIG. 2.

As is clear from FIG. 2, it was shown that as compared to the control (SA) for which no peptide was used, the fluorescence intensity tended to increase when the peptides represented by SEQ ID NOS: 4, 5, 7, and 11 were used (SA-TP24, SA-TP25, SA-TP14, and SA-TP19). This indicates that the mediation of each of the peptides allowed the target protein to be easily and densely immobilized to the $Si_3N_4$ substrate. Therefore, similarly to Example 1, it was revealed that the peptides represented by SEQ ID NOS: 4, 5, 7, and 11 also have a good affinity for the $Si_3N_4$ substrate and are useful for immobilization of the target protein to the $Si_3N_4$ substrate.

Example 3

The peptides represented by SEQ ID NOS: 1 to 11 were investigated for presence/absence of an affinity for a $Si_3N_4$ substrate in accordance with the procedure described below.

1. Procedure 1) 12 g (approximate surface area: 187.4 cm²) of the same $Si_3N_4$ substrate as that in Example 1 was mixed with each PBS solution containing the peptides represented by SEQ ID NOS: 1 to 11, and each solution was shaken at 25° C. and 200 rpm for 2 hours.

2) A portion of the supernatant of each of the solutions was analyzed by HPLC, and the remaining portion of each of the solutions was further mixed with the $Si_3N_4$ substrate. At that time, the amount of the substrate per 1 mL was set at 1.5 g.

3) Step 2) was repeated five times in total.

4) It was determined that a peptide that exhibits a significantly reduced peak area after adsorption has an affinity for the $Si_3N_4$ substrate; therefore, chromatograms before and after adsorption were compared.

In the above step 2), the analysis by HPLC was conducted as follows. First, an HPLC system was started up, and then an A solution and a B solution for HPLC were fed to Lines A and B. Thereafter, the A solution was fed to a column at a flow rate of 1 mL/min to equilibrate the interior of the column. Next, each of the PBS solutions that had not been applied to the experiment yet and the portion of the supernatant collected in the above step 2) was filtered through a pretreatment filter, and 100 µL thereof was fed to the column. The concentration of the B solution was linearly increased in accordance with the program shown in Table 1 below, to elute the peptide from the column. Thereafter, chromatograms before and after adsorption were compared.

The HPLC system, the A solution, the B solution, the pretreatment filter, and the program were as follows.

HPLC System

PU-2089 Quaternary Gradient Pump (manufactured by JASCO International Co., Ltd.)

LC-NetII/ADC (manufactured by JASCO International Co., Ltd.)

MD-2018 Plus Photodiode Array Detector (manufactured by JASCO International Co., Ltd.)

UV-1575 Intelligent UV/VIS Detector (manufactured by JASCO International Co., Ltd.)

TSKgel ODS-100Z 3 µm (column size: 4.6 mm, I.D.: ×15 cm) (manufactured by TOSOH CORPORATION)

A Solution

Ultrapure water (1 L)

TFA (Trifluoroacetic acid, for high-performance liquid chromatograph, manufactured by Wako Pure Chemical Industries, Ltd.) (1 mL) 0.1 v/v %

B Solution

Acetonitrile [Chromasolv, for HPLC, gradient grade, ≥99.9%] (manufactured by Sigma-Aldrich Japan) (1 L)

TFA (for high-performance liquid chromatograph) (1 mL) 0.1 v/v %

Pretreatment Filter

Non-Sterile 4 mm Millex (registered trademark) HV syringe Driven Filter Unit (450 nm) (manufactured by Millipore Corporation)

Program

TABLE 1

| 70-minute program | |
|---|---|
| Time (min) | Acetonitrile (%) |
| 0 | 0 |
| 60 | 50 |
| 65 | 100 |
| 70 | 100 |

2. Results

As a result, it was confirmed from a comparison of the chromatograms before and after adsorption that regardless of which solution was used, the peak area after adsorption was reduced, and thus each of the peptides represented by SEQ ID NOS: 1 to 11 has an affinity for the $Si_3N_4$ substrate. Therefore, it was revealed that the use of peptides having these amino acid sequences makes it possible to increase the density and activity of a target protein, and to render highly controlled orientation of the target protein immobilized to the silicon nitride substrate via these peptides. Furthermore, it was confirmed that the reduction ratio of the peak area was 50% or more. A comparison of the chromatograms also allows one to understand the reduction ratio of the peak area before and after adsorption; i.e., it can be determined that the higher the reduction ratio, the higher the affinity of the peptide for silicon nitride. From the standpoint that the affinity for silicon nitride is higher, it was thought that an exemplary reduction ratio of the peak area is 50% or more, more preferably 70% or more, and yet more preferably 80% or more.

Example 4

The affinity of each peptide for a silicon nitride substrate was examined in accordance with the procedure described below.

1. Procedure

GST fused with each peptide was prepared in the same procedure as Example 1, except that the polypeptides represented by SEQ ID NOS: 6 to 8 and 10 (the polynucleotides having the nucleotide sequences represented by SEQ ID NOS: 17 to 19 and 21) were used instead of the peptides represented by SEQ ID NOS: 1 and 2. In the following, V821 denotes the peptide represented by SEQ ID NO: 6, TP14 denotes the peptide represented by SEQ ID NO: 7, V829 denotes the peptide represented by SEQ ID NO: 8, and CT22 denotes the peptide represented by SEQ ID NO: 10. In addition, the prepared GSTs fused with the respective peptides are denoted by GST-V821, GST-TP14, GST-V829, and GST-CT22, respectively. These GSTs were also obtained by fusing the peptides to the C-terminal region of GST.

Adsorption of the prepared GTS fused with each peptide to a $Si_3N_4$ substrate was evaluated in accordance with the procedure described below. Wild-type GST (wt-GST), to which no peptide was fused, was used as a control.

First, similar to Example 1 described above, GST solutions were prepared using the same PBS as that in Example 1 in such a manner that the wt-GST or GST fused with each peptide was 100 µg/mL (1 cm³). At that time, three types of GST solutions having different levels of ionic strength (ionic strength: 0.075, 0.15, and 0.3) were prepared. The Si3N4 substrate (sensor chip) was attached to an RIfS sensor (MI-Affinity, manufactured by Konica Minolta, Inc.), and the PBS was fed at a flow rate of 100 µL/min to equilibrate the interior of a flow path. 100 µL of each GST solution was fed to the sensor chip, and the value of the detected wavelength shift amount ($\Delta\lambda$(nm)) was monitored. The value of the wavelength shift amount obtained when adsorption equilibrium was established by two or three injections was evaluated as an index of the amount of adsorption.

2. Results

Figure 3:
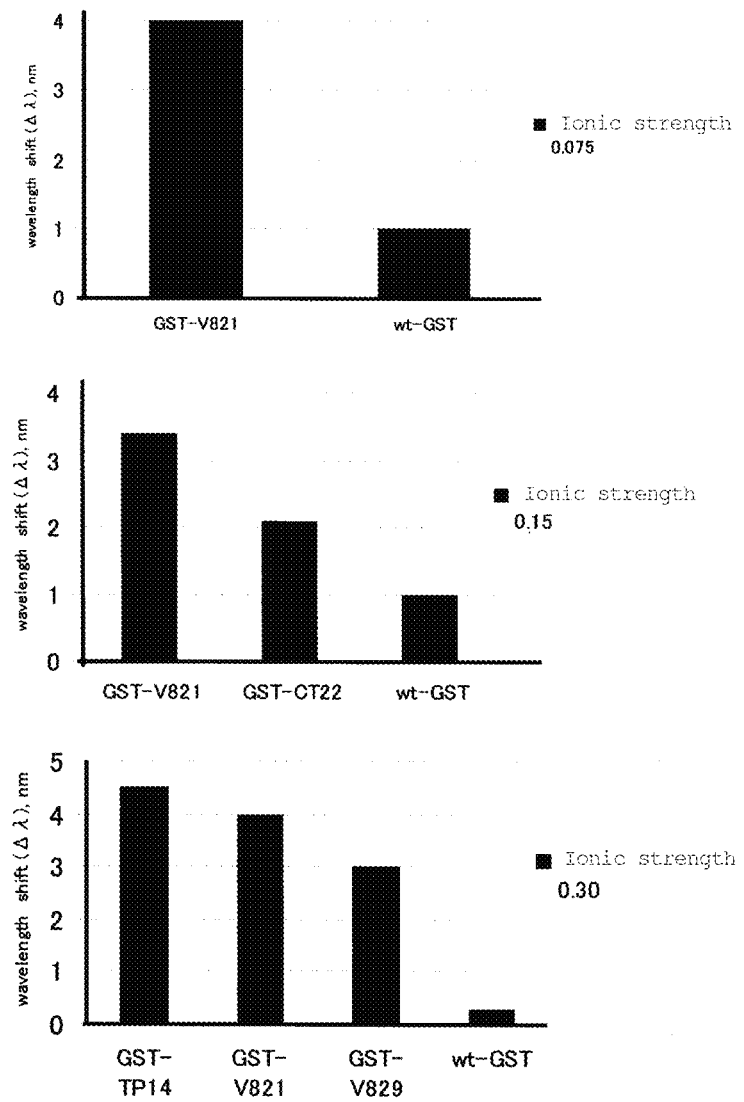
FIG. 3 indicates that the peptide of the present invention has an affinity for a silicon nitride substrate. The sequences represented in the figures are V821 (SEQ ID NO: 6), TP14 (SEQ ID NO: 7), and V829 (SEQ ID NO: 8).

The results are shown in FIG. 3. FIG. 3 shows the adsorption density to the $Si_3N_4$ substrate. As is clear from FIG. 3, with respect to wt-GST, significant improvement in the adsorption density to the $Si_3N_4$ substrate was observed for any of GST-V821, GST-CT22, GST-TP14, and GST-V829. This indicates that the introduction of the peptides represented by SEQ ID NOS: 6 to 8 and 10 allowed GTS to be easily and densely immobilized to the $Si_3N_4$ substrate. Therefore, it was revealed that any of the peptides represented by SEQ ID NOS: 6 to 8 and 10 has a good affinity for the $Si_3N_4$ substrate and is useful for immobilization of a target protein to the $Si_3N_4$ substrate. In addition, since it was possible to introduce the peptide to a desired position of GST, and improvement in the adsorption density was observed for the obtained peptide-fused GST, it was revealed that the use of these peptides makes it possible to maintain the activity and control the orientation of the target protein. Moreover, although not indicated here, the same tendency was also observed when each of the peptides represented by SEQ ID NOS: 3 to 5, 9, and 11 was introduced to GTS. Furthermore, FIG. 3 shows the results at pH 7, but the same tendency was also observed in experiments conducted at pH 9.

Example 5

The affinity of GST-TP14, GST-V821, GST-V829, and GST-CT22 constructed as described above for a $Si_3N_4$ substrate were examined using an instrument different from that in Example 4 in accordance with the procedure described below.

1. Procedure

GST solutions were prepared in the same manner as in Example 4 using PBS in such a manner that the wt-GST or GST fused with each peptide was 0.1 µg/mL, 1 µg/mL, 10 µg/mL, and 100 µg/mL (1 cm³). Also in the present example, solutions having different levels of ionic strength (ionic strength: 0.075, 0.15, and 0.3) were prepared for the GST solution with each concentration. The $Si_3N_4$ substrate (sensor chip) was attached to an RIfS sensor (Wacaris, manufactured by Nissha Printing Co., Ltd.), and the PBS was fed at a flow rate of 100 µL/min to equilibrate the interior of a flow path. 100 µL of each of the GST solutions was fed to the sensor chip, and the value of the detected wavelength shift amount ($\Delta\lambda$(nm)) was monitored. The value of the wavelength shift amount obtained when adsorption equilibrium was established by two or three injections was evaluated as an index of the amount of adsorption.

2. Results

Figure 4:
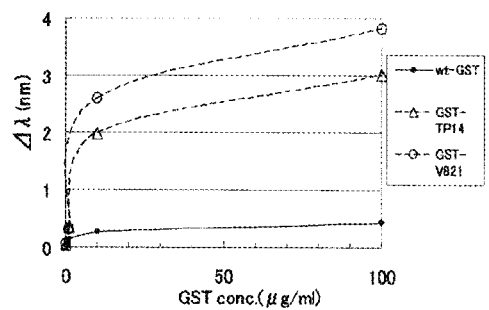
FIG. 4 indicates that the peptide of the present invention has an affinity for a silicon nitride substrate. The sequences represented in the figure are V821 (SEQ ID NO: 6), TP14 (SEQ ID NO: 7), V829 (SEQ ID NO: 8), and CT22 (SEQ ID NO: 10).
Figure 4:
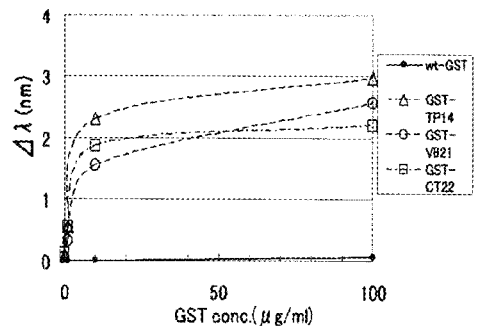
Figure 4:
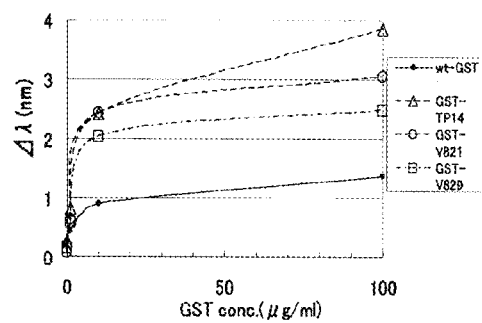

The results are shown in FIG. 4. As is clear from FIG. 4, also in the present example, regardless of which peptide-fused GST was used, significant improvement in the amount of adsorption was observed as compared to wt-GST. In addition, although not indicated here, the same tendency was also observed when each of the peptides represented by SEQ ID NOS: 3 to 5, 9, and 11 was introduced to GTS.

Example 6

In addition to examining the adsorption density of a peptide-fused GST, it was examined whether GTS forming the peptide-fused GST immobilized to a $Si_3N_4$ substrate maintains the original GTS activity.

1. Procedure

1) GST solutions were prepared using PBS in such a manner that wt-GST, GST-TP14, or GST-V821 was 100 µg/mL (1 cm³), and 2 mL of each GST solution was brought into contact with 2 g (surface area: 31.2 cm², area/volume: 31.2 cm$^{-1}$) of the $Si_3N_4$ substrate and incubated at 25° C. for 2 hours.

2) Each supernatant was collected, and the GST concentration in each of the supernatants was determined by a DC Protein Assay.

3) The amount of adsorption was calculated based on the difference in GST concentration before and after adsorption, and the adsorption density was calculated by dividing the amount of adsorption by the contact area (31.2 cm²).

4) Next, the $Si_3N_4$ substrate was washed three times with PBS and once with a 0.1-M potassium phosphate aqueous solution (pH 6.5), and the solution was completely removed by an aspirator.

5) 3 mL of a 0.1-M potassium phosphate aqueous solution containing 1 mM of CDNB and 1 mM of GSH was added, the change in absorbance at 340 nm was measured with the trace spectrophotometer Nano Drop (manufactured by Thermo Fisher Scientific Inc.) every 30 seconds with stirring at 25° C. and 300 rpm, and the absorbance change (min$^{-1}$·cm$^{-1}$) was calculated. The amount of product formed in 1 minute was calculated based on the molar absorbance coefficient of the product CDNB-GSH, $\epsilon$=9.6 mM$^{-1}$·cm$^{-1}$, and was defined as an enzyme activity. 1 U is the enzyme amount required to prepare 1 mmol of CDNB-GSH in 1 minute.

6) The detected enzyme activity was divided by the area of the $Si_3N_4$ substrate to calculate the enzyme activity mU/cm$^{-2}$ per unit area.

2. Results

Figure 5:
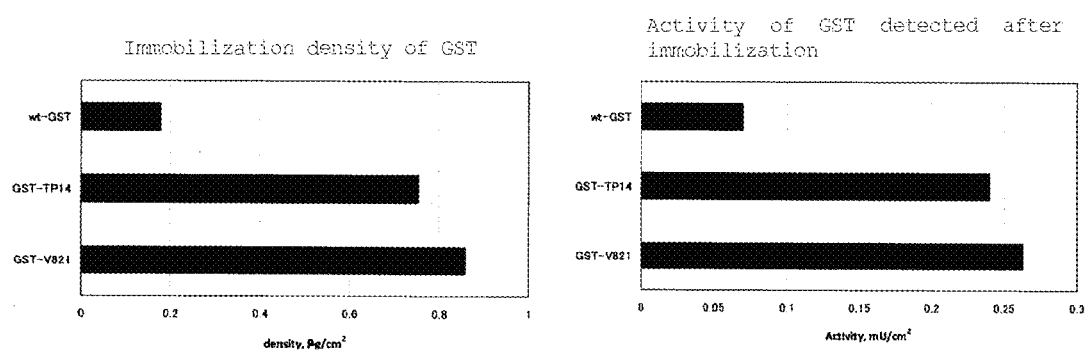
FIG. 5 indicates that a GST-fused peptide has an affinity for a silicon nitride substrate, and GST immobilized to the substrate excellently exhibited its inherent activity. The sequences represented in the figure are V821 (SEQ ID NO: 6) and TP14 (SEQ ID NO: 7).

The results are shown in FIG. 5. As is clear from the results, GST was densely immobilized to the $Si_3N_4$ substrate, and the GTS forming the peptide-fused GST maintained the original GTS activity even after the peptide-fused GST was immobilized to the $Si_3N_4$ substrate. This confirmed that linking the target protein with a peptide having an affinity for $Si_3N_4$ allows the target protein to be densely immobilized on the $Si_3N_4$ substrate and also allows the target protein to exert high activity even after the target protein is immobilized. Although not indicated here, the same tendency was also observed when each of the peptides represented by SEQ ID NOS: 3 to 5 and 9 to 11 was introduced to GTS.

Example 7

Each of the peptides represented by SEQ ID NOS: 23 to 35 was investigated for presence/absence of an affinity for a $Si_3N_4$ substrate in accordance with the procedure described below.

1. Procedure 1) 10.5 g (approximate surface area: 164.02 cm$^2$) of the same $Si_3N_4$ substrate as that in Example 1 was mixed with each of the PBS solutions containing the peptides represented by SEQ ID NOS: 23 to 35, and each of the solutions was shaken at 25° C. and 200 rpm for 2 hours.

2) A portion of the supernatant of each solution was analyzed by HPLC, and the remaining portion of each of the solutions was further mixed with the $Si_3N_4$ substrate. At that time, the amount of the substrate per 1 mL was set at 1.5 g.

3) Step 2) was repeated six times in total.

4) It can be determined that a peptide that exhibits a significantly reduced peak area after adsorption has an affinity for the $Si_3N_4$ substrate; therefore, chromatograms before and after adsorption were compared.

In the above step 2), the analysis by HPLC was conducted in the same manner as in Example 3 to elute the peptide from the column. Thereafter, chromatograms before and after adsorption were compared.

2. Results

As a result, it was confirmed from a comparison of the chromatograms before and after adsorption that regardless of which solution was used, the peak area after adsorption was reduced, and thus each of the peptides represented by SEQ ID NOS: 23 to 35 has an affinity for the $Si_3N_4$ substrate. Therefore, it was revealed that the use of peptides having these amino acid sequences makes it possible to increase the density and activity of a target protein, and to render highly controlled orientation of the target protein immobilized to the silicon nitride substrate via these peptides. Furthermore, it was confirmed that the reduction ratio of the peak area was 50% or more.

Example 8

The affinity of each of the peptides represented by SEQ ID NOS: 23, 24, and 26 for a $Si_3N_4$ substrate was examined in accordance with the procedure described below.

1. Procedure

Construction of Isocitrate Dehydrogenase (ISD) Expression Vector

An ISD expression vector was collected and purified in the same manner as in Example 1, except that the isocitrate dehydrogenase (ISD) gene was used instead of the ELN gene.

Construction of GST Expression Vector pGEX-3X

In the present example, the following experiment was conducted using the same vector as that purified in Example 1.

Preparation of GSTs Fused with Peptides and Adsorption of Peptide-Fused GSTs to $Si_3N_4$ Substrate GTS fused with each peptide was prepared in the same procedure as in Example 5, except that the peptides represented by SEQ ID NOS: 23, 24, and 26 were used instead of the peptides represented by SEQ ID NOS: 6 to 8 and 10. In the following, SIN3 denotes the peptide represented by SEQ ID NO: 23, SIN4 denotes the peptide represented by SEQ ID NO: 24, and TP4 denotes the peptide represented by SEQ ID NO: 26. The prepared GTSs fused with the respective peptides are denoted by GST-SIN3, GST-SIN4, and GST-TP4, respectively. The amount of adsorption of the prepared GTS fused with each peptide, to the $Si_3N_4$ substrate, was evaluated with the same procedure as in Example 5 using an RIfS sensor (Wacaris, manufactured by Nissha Printing Co., Ltd.) having the $Si_3N_4$ substrate (sensor chip) attached thereto. As a control, wild-type GST (wt-GST) to which no peptide was fused, was used. The GST concentration was set at 100 ug/mL for wt-GST and at 50 ug/mL for each peptide-fused GTS.

2. Results

Figure 6:
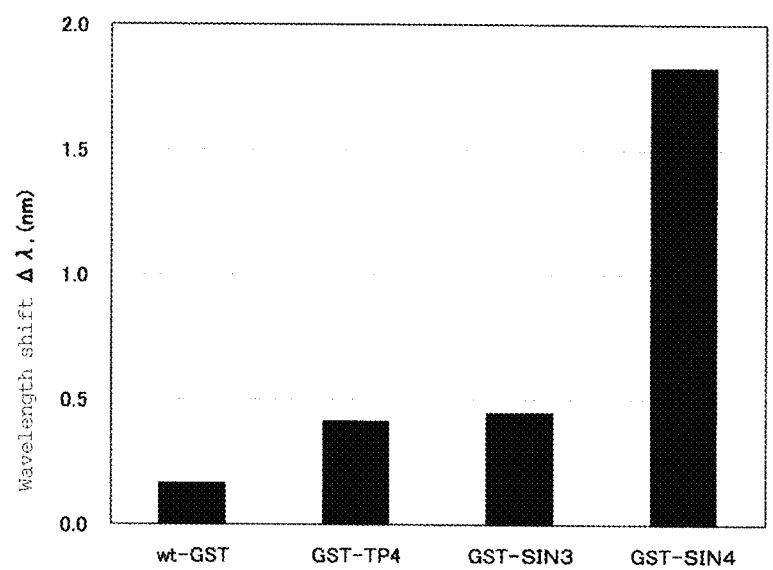
FIG. 6 indicates that the peptide of the present invention has an affinity for a silicon nitride substrate. The sequences represented in the figure are SIN3 (SEQ ID NO: 23), SIN4 (SEQ ID NO: 24), AND TP4 (SEQ ID NO: 26).

The results are shown in FIG. 6. As is clear from FIG. 6, it was observed that for any peptide-fused GST of GST-SIN3, GST-SIN4, and GST-TP4, improvement in the adsorption density to the $Si_3N_4$ substrate was observed as compared to wt-GST. In particular, although the concentration of wt-GST is double that of each of the GST-SIN3, GST-SIN4, and GST-TP4, significant improvement in the amount of adsorption was observed for GST-SIN3, GST-SIN4, and GST-TP4. This result indicates that the introduction of the peptide represented by any of SEQ ID NOS: 23, 24, and 26 also allowed GTS to be easily and densely immobilized to the $Si_3N_4$ substrate. Therefore, it was revealed that the peptides represented by SEQ ID NOS: 23, 24, and 26 also have a good affinity for the $Si_3N_4$ substrate and are useful for immobilization of a target protein to the $Si_3N_4$ substrate. In addition, since it was possible to introduce each of these peptides to a desired position of GST and improvement in the adsorption density was observed for the obtained peptide-fused GST as described above, it was revealed that the peptides also enabled maintenance of the activity of and orientation control of the target protein. Moreover, the same tendency was also observed for GST fused with each of the peptides represented SEQ ID NOS: 25 and 27 to 35.

Sequence List
PCT_silicon nitride(Si3N_20130212_140830_1.txt

The invention claimed is:

1. A silicon nitride substrate comprising a peptide having an affinity for silicon nitride bonded thereto, the peptide consisting of any one of SEQ ID NOS: 1 to 11.

2. A silicon nitride substrate comprising a target protein immobilized to the silicon nitride substrate via a peptide of any one of SEQ ID NOS: 1 to 11, the peptide having an affinity for silicon nitride, and the target protein selected from the group consisting of an antibody and a lectin.

3. A method for immobilizing a target protein to a silicon nitride substrate comprising: contacting a silicon nitride substrate with the target protein fused to a peptide having an affinity for silicon nitride, the peptide consisting of any one of SEQ ID NOS: 1 to 11, the target protein selected from the group consisting of an antibody and a lectin.

* * * * *

SEQUENCE LISTING

<160> NUMBER OF SEQ ID NOS: 48

<210> SEQ ID NO 1
<211> LENGTH: 68
<212> TYPE: PRT
<213> ORGANISM: Escherichia coli

<400> SEQUENCE: 1

```
Leu Leu Ser Gln Tyr Asp Phe Pro Gly Asp Asp Thr Pro Ile Val Arg
1               5                   10                  15

Gly Ser Ala Leu Lys Ala Leu Glu Gly Asp Ala Glu Trp Glu Ala Lys
            20                  25                  30

Ile Leu Glu Leu Ala Gly Phe Leu Asp Ser Tyr Ile Pro Glu Pro Glu
        35                  40                  45

Arg Ala Ile Asp Lys Pro Phe Leu Leu Pro Ile Glu Asp Val Phe Ser
    50                  55                  60

Ile Ser Gly Arg
65
```

<210> SEQ ID NO 2
<211> LENGTH: 78
<212> TYPE: PRT
<213> ORGANISM: Escherichia coli

<400> SEQUENCE: 2

```
Gly Gly Arg His Thr Pro Phe Phe Lys Gly Tyr Arg Pro Gln Phe Tyr
1               5                   10                  15

Phe Arg Thr Thr Asp Val Thr Gly Thr Ile Glu Leu Pro Glu Gly Val
            20                  25                  30

Glu Met Val Met Pro Gly Asp Asn Ile Lys Met Val Val Thr Leu Ile
        35                  40                  45

His Pro Ile Ala Met Asp Asp Gly Leu Arg Phe Ala Ile Arg Glu Gly
    50                  55                  60

Gly Arg Thr Val Gly Ala Gly Val Val Ala Lys Val Leu Ser
65                  70                  75
```

<210> SEQ ID NO 3
<211> LENGTH: 24
<212> TYPE: PRT
<213> ORGANISM: Escherichia coli

<400> SEQUENCE: 3

```
Leu Leu Ser Gln Tyr Asp Phe Pro Gly Asp Asp Thr Pro Ile Val Arg
1               5                   10                  15

Gly Ser Ala Leu Lys Ala Leu Glu
            20
```

<210> SEQ ID NO 4
<211> LENGTH: 17
<212> TYPE: PRT
<213> ORGANISM: Escherichia coli

<400> SEQUENCE: 4

```
Ile Leu Glu Leu Ala Gly Phe Leu Asp Ser Tyr Ile Pro Glu Pro Glu
1               5                   10                  15

Arg
```

<210> SEQ ID NO 5
<211> LENGTH: 19
<212> TYPE: PRT
<213> ORGANISM: Escherichia coli

<400> SEQUENCE: 5

```
Ala Ile Asp Lys Pro Phe Leu Leu Pro Ile Glu Asp Val Phe Ser Ile
1               5                   10                  15

Ser Gly Arg
```

```
<210> SEQ ID NO 6
<211> LENGTH: 27
<212> TYPE: PRT
<213> ORGANISM: Escherichia coli

<400> SEQUENCE: 6

Gly Gly Arg His Thr Pro Phe Phe Lys Gly Tyr Arg Pro Gln Phe Tyr
1               5                   10                  15

Phe Arg Thr Thr Asp Val Thr Gly Thr Ile Glu
            20                  25

<210> SEQ ID NO 7
<211> LENGTH: 9
<212> TYPE: PRT
<213> ORGANISM: Escherichia coli

<400> SEQUENCE: 7

Gly Tyr Arg Pro Gln Phe Tyr Phe Arg
1               5

<210> SEQ ID NO 8
<211> LENGTH: 30
<212> TYPE: PRT
<213> ORGANISM: Escherichia coli

<400> SEQUENCE: 8

Met Val Met Pro Gly Asp Asn Ile Lys Met Val Val Thr Leu Ile His
1               5                   10                  15

Pro Ile Ala Met Asp Asp Gly Leu Arg Phe Ala Ile Arg Glu
            20                  25                  30

<210> SEQ ID NO 9
<211> LENGTH: 16
<212> TYPE: PRT
<213> ORGANISM: Escherichia coli

<400> SEQUENCE: 9

Met Val Val Thr Leu Ile His Pro Ile Ala Met Asp Asp Gly Leu Arg
1               5                   10                  15

<210> SEQ ID NO 10
<211> LENGTH: 19
<212> TYPE: PRT
<213> ORGANISM: Escherichia coli

<400> SEQUENCE: 10

Phe Ala Ile Arg Glu Gly Gly Arg Thr Val Gly Ala Gly Val Val Ala
1               5                   10                  15

Lys Val Leu

<210> SEQ ID NO 11
<211> LENGTH: 12
<212> TYPE: PRT
<213> ORGANISM: Escherichia coli

<400> SEQUENCE: 11

Thr Val Gly Ala Gly Val Val Ala Lys Val Leu Ser
1               5                   10

<210> SEQ ID NO 12
<211> LENGTH: 204
<212> TYPE: DNA
<213> ORGANISM: Escherichia coli
```

<400> SEQUENCE: 12
cttctgtctc agtacgactt cccgggcgac gacactccga tcgttcgtgg ttctgctctg    60
aaagcgctgg aaggcgacgc agagtgggaa gcgaaaatcc tggaactggc tggcttcctg   120
gattcttaca ttccggaacc agagcgtgcg attgacaagc cgttcctgct gccgatcgaa   180
gacgtattct ccatctccgg tcgt                                          204

<210> SEQ ID NO 13
<211> LENGTH: 234
<212> TYPE: DNA
<213> ORGANISM: Escherichia coli

<400> SEQUENCE: 13
ggcggccgtc atactccgtt cttcaaaggc taccgtccgc agttctactt ccgtactact    60
gacgtgactg gtaccatcga actgccggaa ggcgtagaga tggtaatgcc gggcgacaac   120
atcaaaatgg ttgttaccct gatccacccg atcgcgatgg acgacggtct gcgtttcgca   180
atccgtgaag gcggccgtac cgttggcgcg ggcgttgtag caaaagttct gagc         234

<210> SEQ ID NO 14
<211> LENGTH: 72
<212> TYPE: DNA
<213> ORGANISM: Escherichia coli

<400> SEQUENCE: 14
cttctgtctc agtacgactt cccgggcgac gacactccga tcgttcgtgg ttctgctctg    60
aaagcgctgg aa                                                        72

<210> SEQ ID NO 15
<211> LENGTH: 51
<212> TYPE: DNA
<213> ORGANISM: Escherichia coli

<400> SEQUENCE: 15
atcctggaac tggctggctt cctggattct tacattccgg aaccagagcg t             51

<210> SEQ ID NO 16
<211> LENGTH: 57
<212> TYPE: DNA
<213> ORGANISM: Escherichia coli

<400> SEQUENCE: 16
gcgattgaca agccgttcct gctgccgatc gaagacgtat tctccatctc cggtcgt       57

<210> SEQ ID NO 17
<211> LENGTH: 81
<212> TYPE: DNA
<213> ORGANISM: Escherichia coli

<400> SEQUENCE: 17
ggcggccgtc atactccgtt cttcaaaggc taccgtccgc agttctactt ccgtactact    60
gacgtgactg gtaccatcga a                                              81

<210> SEQ ID NO 18
<211> LENGTH: 27
<212> TYPE: DNA
<213> ORGANISM: Escherichia coli

<400> SEQUENCE: 18

```
ggctaccgtc cgcagttcta cttccgt                                          27

<210> SEQ ID NO 19
<211> LENGTH: 90
<212> TYPE: DNA
<213> ORGANISM: Escherichia coli

<400> SEQUENCE: 19
atggtaatgc cgggcgacaa catcaaaatg gttgttaccc tgatccaccc gatcgcgatg     60
gacgacggtc tgcgtttcgc aatccgtgaa                                      90

<210> SEQ ID NO 20
<211> LENGTH: 48
<212> TYPE: DNA
<213> ORGANISM: Escherichia coli

<400> SEQUENCE: 20
atggttgtta ccctgatcca cccgatcgcg atggacgacg gtctgcgt                  48

<210> SEQ ID NO 21
<211> LENGTH: 57
<212> TYPE: DNA
<213> ORGANISM: Escherichia coli

<400> SEQUENCE: 21
ttcgcaatcc gtgaaggcgg ccgtaccgtt ggcgcgggcg ttgtagcaaa agttctg        57

<210> SEQ ID NO 22
<211> LENGTH: 36
<212> TYPE: DNA
<213> ORGANISM: Escherichia coli

<400> SEQUENCE: 22
accgttggcg cgggcgttgt agcaaaagtt ctgagc                               36

<210> SEQ ID NO 23
<211> LENGTH: 53
<212> TYPE: PRT
<213> ORGANISM: Escherichia coli

<400> SEQUENCE: 23

Leu Asn Val Pro Glu Asn Pro Ile Ile Pro Tyr Ile Glu Gly Asp Gly
1               5                   10                  15

Ile Gly Val Asp Val Thr Pro Ala Met Leu Lys Val Val Asp Ala Ala
            20                  25                  30

Val Glu Lys Ala Tyr Lys Gly Glu Arg Lys Ile Ser Trp Met Glu Ile
        35                  40                  45

Tyr Thr Gly Glu Lys
    50

<210> SEQ ID NO 24
<211> LENGTH: 58
<212> TYPE: PRT
<213> ORGANISM: Escherichia coli

<400> SEQUENCE: 24

Ala Thr His Gly Thr Ala Pro Lys Tyr Ala Gly Gln Asp Lys Val Asn
1               5                   10                  15

Pro Gly Ser Ile Ile Leu Ser Ala Glu Met Met Leu Arg His Met Gly
            20                  25                  30

Trp Thr Glu Ala Ala Asp Leu Ile Val Lys Gly Met Glu Gly Ala Ile
```

```
              35                  40                  45

Asn Ala Lys Thr Val Thr Tyr Asp Phe Glu
    50                  55

<210> SEQ ID NO 25
<211> LENGTH: 6
<212> TYPE: PRT
<213> ORGANISM: Escherichia coli

<400> SEQUENCE: 25

Asp Leu Ile Arg Glu Tyr
1               5

<210> SEQ ID NO 26
<211> LENGTH: 11
<212> TYPE: PRT
<213> ORGANISM: Escherichia coli

<400> SEQUENCE: 26

His Pro Glu Leu Thr Asp Met Val Ile Phe Arg
1               5                   10

<210> SEQ ID NO 27
<211> LENGTH: 18
<212> TYPE: PRT
<213> ORGANISM: Escherichia coli

<400> SEQUENCE: 27

Leu Ile Asp Gly Gly Pro Trp Leu Lys Val Lys Asn Pro Asn Thr Gly
1               5                   10                  15

Lys Glu

<210> SEQ ID NO 28
<211> LENGTH: 20
<212> TYPE: PRT
<213> ORGANISM: Escherichia coli

<400> SEQUENCE: 28

Leu Asn Val Pro Glu Asn Pro Ile Ile Pro Tyr Ile Glu Gly Asp Gly
1               5                   10                  15

Ile Gly Val Asp
            20

<210> SEQ ID NO 29
<211> LENGTH: 27
<212> TYPE: PRT
<213> ORGANISM: Escherichia coli

<400> SEQUENCE: 29

Leu Asn Val Pro Glu Asn Pro Ile Ile Pro Tyr Ile Glu Gly Asp Gly
1               5                   10                  15

Ile Gly Val Asp Val Thr Pro Ala Met Leu Lys
            20                  25

<210> SEQ ID NO 30
<211> LENGTH: 12
<212> TYPE: PRT
<213> ORGANISM: Escherichia coli

<400> SEQUENCE: 30

Lys Ile Ser Trp Met Glu Ile Tyr Thr Gly Glu Lys
1               5                   10
```

-continued

<210> SEQ ID NO 31
<211> LENGTH: 25
<212> TYPE: PRT
<213> ORGANISM: Escherichia coli

<400> SEQUENCE: 31

Ala Thr His Gly Thr Ala Pro Lys Tyr Ala Gly Gln Asp Lys Val Asn
1               5                   10                  15

Pro Gly Ser Ile Ile Leu Ser Ala Glu
            20                  25

<210> SEQ ID NO 32
<211> LENGTH: 21
<212> TYPE: PRT
<213> ORGANISM: Escherichia coli

<400> SEQUENCE: 32

Val Asn Pro Gly Ser Ile Ile Leu Ser Ala Glu Met Met Leu Arg His
1               5                   10                  15

Met Gly Trp Thr Glu
            20

<210> SEQ ID NO 33
<211> LENGTH: 32
<212> TYPE: PRT
<213> ORGANISM: Escherichia coli

<400> SEQUENCE: 33

Met Leu Arg His Met Gly Trp Thr Glu Ala Ala Asp Leu Ile Val Lys
1               5                   10                  15

Gly Met Glu Gly Ala Ile Asn Ala Lys Thr Val Thr Tyr Asp Phe Glu
            20                  25                  30

<210> SEQ ID NO 34
<211> LENGTH: 13
<212> TYPE: PRT
<213> ORGANISM: Escherichia coli

<400> SEQUENCE: 34

His Met Gly Trp Thr Glu Ala Ala Asp Leu Ile Val Lys
1               5                   10

<210> SEQ ID NO 35
<211> LENGTH: 15
<212> TYPE: PRT
<213> ORGANISM: Escherichia coli

<400> SEQUENCE: 35

Val Asn Pro Gly Ser Ile Ile Leu Ser Ala Glu Met Met Leu Arg
1               5                   10                  15

<210> SEQ ID NO 36
<211> LENGTH: 159
<212> TYPE: DNA
<213> ORGANISM: Escherichia coli

<400> SEQUENCE: 36
ctcaacgttc ctgaaaatcc gattatccct tacattgaag gtgatggaat cggtgtagat      60
gtaaccccag ccatgctgaa agtggtcgac gctgcagtcg agaaagccta taaggcgag     120 cgtaaaatct cctggatgga aatttacacc ggtgaaaaa                           159

<210> SEQ ID NO 37
<211> LENGTH: 174
<212> TYPE: DNA
<213> ORGANISM: Escherichia coli

<400> SEQUENCE: 37

```
gccacccacg gtactgcgcc gaaatatgcc ggtcaggaca aagtaaatcc tggctctatt      60
attctctccg ctgagatgat gctgcgccac atgggttgga ccgaagcggc tgacttaatt     120
gttaaaggta tggaaggcgc aatcaacgcg aaaaccgtaa cctatgactt cgag            174
```

<210> SEQ ID NO 38
<211> LENGTH: 18
<212> TYPE: DNA
<213> ORGANISM: Escherichia coli

<400> SEQUENCE: 38

```
gatctgattc gtgaatat                                                    18
```

<210> SEQ ID NO 39
<211> LENGTH: 33
<212> TYPE: DNA
<213> ORGANISM: Escherichia coli

<400> SEQUENCE: 39

```
caccctgaac tgaccgatat ggttatcttc cgt                                   33
```

<210> SEQ ID NO 40
<211> LENGTH: 54
<212> TYPE: DNA
<213> ORGANISM: Escherichia coli

<400> SEQUENCE: 40

```
ctgatcgacg gtggcccgtg gctgaaagtt aaaaacccga acactggcaa agag            54
```

<210> SEQ ID NO 41
<211> LENGTH: 60
<212> TYPE: DNA
<213> ORGANISM: Escherichia coli

<400> SEQUENCE: 41

```
ctcaacgttc ctgaaaatcc gattatccct tacattgaag gtgatggaat cggtgtagat      60
```

<210> SEQ ID NO 42
<211> LENGTH: 81
<212> TYPE: DNA
<213> ORGANISM: Escherichia coli

<400> SEQUENCE: 42

```
ctcaacgttc ctgaaaatcc gattatccct tacattgaag gtgatggaat cggtgtagat      60
gtaaccccag ccatgctgaa a                                                81
```

<210> SEQ ID NO 43
<211> LENGTH: 36
<212> TYPE: DNA
<213> ORGANISM: Escherichia coli

<400> SEQUENCE: 43

```
aaaatctcct ggatggaaat ttacaccggt gaaaaa                                36
```

<210> SEQ ID NO 44
<211> LENGTH: 75
<212> TYPE: DNA

```
<213> ORGANISM: Escherichia coli

<400> SEQUENCE: 44
gccacccacg gtactgcgcc gaaatatgcc ggtcaggaca aagtaaatcc tggctctatt    60
attctctccg ctgag                                                    75

<210> SEQ ID NO 45
<211> LENGTH: 63
<212> TYPE: DNA
<213> ORGANISM: Escherichia coli

<400> SEQUENCE: 45
gtaaatcctg gctctattat tctctccgct gagatgatgc tgcgccacat gggttggacc    60
gaa                                                                 63

<210> SEQ ID NO 46
<211> LENGTH: 96
<212> TYPE: DNA
<213> ORGANISM: Escherichia coli

<400> SEQUENCE: 46
atgctgcgcc acatgggttg gaccgaagcg gctgacttaa ttgttaaagg tatggaaggc    60
gcaatcaacg cgaaaaccgt aacctatgac ttcgag                             96

<210> SEQ ID NO 47
<211> LENGTH: 39
<212> TYPE: DNA
<213> ORGANISM: Escherichia coli

<400> SEQUENCE: 47
cacatgggtt ggaccgaagc ggctgactta attgttaaa                          39

<210> SEQ ID NO 48
<211> LENGTH: 45
<212> TYPE: DNA
<213> ORGANISM: Escherichia coli

<400> SEQUENCE: 48
gtaaatcctg gctctattat tctctccgct gagatgatgc tgcgc                   45
```